United States Patent
Stahmann

(10) Patent No.: US 10,894,163 B2
(45) Date of Patent: Jan. 19, 2021

(54) LCP BASED PREDICTIVE TIMING FOR CARDIAC RESYNCHRONIZATION

(71) Applicant: CARDIAC PACEMAKERS, INC., St. Paul, MN (US)

(72) Inventor: Jeffrey E. Stahmann, Ramsey, MN (US)

(73) Assignee: CARDIAC PACEMAKERS, INC., St. Paul (MN)

( * ) Notice: Subject to any disclaimer, the term of this patent is extended or adjusted under 35 U.S.C. 154(b) by 292 days.

(21) Appl. No.: 15/805,239

(22) Filed: Nov. 7, 2017

(65) Prior Publication Data
US 2018/0140848 A1  May 24, 2018

Related U.S. Application Data

(60) Provisional application No. 62/424,582, filed on Nov. 21, 2016.

(51) Int. Cl.
*A61N 1/36* (2006.01)
*A61N 1/365* (2006.01)
(Continued)

(52) U.S. Cl.
CPC ....... *A61N 1/36585* (2013.01); *A61N 1/0587* (2013.01); *A61N 1/3622* (2013.01);
(Continued)

(58) Field of Classification Search
CPC .............. A61N 1/36585; A61N 1/3756; A61N 1/37235; A61N 1/36507; A61N 1/3627;
(Continued)

(56) References Cited

U.S. PATENT DOCUMENTS 3,835,864 A    9/1974   Rasor et al.
3,943,936 A    3/1976   Rasor et al.
(Continued)

FOREIGN PATENT DOCUMENTS

AU    2008279789 B2    10/2011
AU    2008329620 B2    5/2014
(Continued)

OTHER PUBLICATIONS

US 8,886,318 B2, 11/2014, Jacobson et al. (withdrawn)
(Continued)

*Primary Examiner* — Amanda K Hulbert
*Assistant Examiner* — Natasha Patel
(74) *Attorney, Agent, or Firm* — Seager, Tufte & Wickhem LLP

(57) ABSTRACT

Methods, systems and devices for providing cardiac resynchronization therapy (CRT) to a patient using a leadless cardiac pacemaker (LCP) implanted in or proximate the left ventricle of a patient. A setup phase is used to establish parameters in the therapy delivery. In operation, the method and/or device will sense at least one non-paced cardiac cycle to determine a native R-R interval, and then delivers a synchronization pace at an interval less than the native R-R interval followed by a plurality of pace therapies delivered at the R-R interval or a modification thereof.

11 Claims, 14 Drawing Sheets

(51) Int. Cl.
    *A61N 1/368*    (2006.01)
    *A61N 1/362*    (2006.01)
    *A61N 1/372*    (2006.01)
    *A61N 1/05*     (2006.01)
    *A61N 1/375*    (2006.01)

(52) U.S. Cl.
    CPC ......... *A61N 1/3627* (2013.01); *A61N 1/3682* (2013.01); *A61N 1/36507* (2013.01); *A61N 1/3756* (2013.01); *A61N 1/37235* (2013.01); *A61N 1/37288* (2013.01); *A61N 1/37512* (2017.08)

(58) Field of Classification Search
    CPC .............. A61N 1/37512; A61N 1/3682; A61N 1/3622; A61N 1/0587; A61N 1/37288
    See application file for complete search history.

(56) References Cited

U.S. PATENT DOCUMENTS

| | | |
|---|---|---|
| 4,142,530 A | 3/1979 | Wittkampf |
| 4,151,513 A | 4/1979 | Menken et al. |
| 4,157,720 A | 6/1979 | Greatbatch |
| RE30,366 E | 8/1980 | Rasor et al. |
| 4,243,045 A | 1/1981 | Maas |
| 4,250,884 A | 2/1981 | Hartlaub et al. |
| 4,256,115 A | 3/1981 | Bilitch |
| 4,263,919 A | 4/1981 | Levin |
| 4,310,000 A | 1/1982 | Lindemans |
| 4,312,354 A | 1/1982 | Walters |
| 4,323,081 A | 4/1982 | Wiebusch |
| 4,357,946 A | 11/1982 | Dutcher et al. |
| 4,365,639 A | 12/1982 | Goldreyer |
| 4,440,173 A | 4/1984 | Hudziak et al. |
| 4,476,868 A | 10/1984 | Thompson |
| 4,522,208 A | 6/1985 | Buffet |
| 4,537,200 A | 8/1985 | Widrow |
| 4,556,063 A | 12/1985 | Thompson et al. |
| 4,562,841 A | 1/1986 | Brockway et al. |
| 4,593,702 A | 6/1986 | Kepski et al. |
| 4,593,955 A | 6/1986 | Leiber |
| 4,630,611 A | 12/1986 | King |
| 4,635,639 A | 1/1987 | Hakala et al. |
| 4,674,508 A | 6/1987 | DeCote |
| 4,712,554 A | 12/1987 | Garson |
| 4,729,376 A | 3/1988 | DeCote |
| 4,754,753 A | 7/1988 | King |
| 4,759,366 A | 7/1988 | Callaghan |
| 4,776,338 A | 10/1988 | Lekholm et al. |
| 4,787,389 A | 11/1988 | Tarjan |
| 4,793,353 A | 12/1988 | Borkan |
| 4,819,662 A | 4/1989 | Heil et al. |
| 4,858,610 A | 8/1989 | Callaghan et al. |
| 4,886,064 A | 12/1989 | Strandberg |
| 4,887,609 A | 12/1989 | Cole, Jr. |
| 4,928,688 A | 5/1990 | Mower |
| 4,967,746 A | 11/1990 | Vandegriff |
| 4,987,897 A | 1/1991 | Funke |
| 4,989,602 A | 2/1991 | Sholder et al. |
| 5,012,806 A | 5/1991 | De Bellis |
| 5,036,849 A | 8/1991 | Hauck et al. |
| 5,040,534 A | 8/1991 | Mann et al. |
| 5,058,581 A | 10/1991 | Silvian |
| 5,078,134 A | 1/1992 | Heilman et al. |
| 5,109,845 A | 5/1992 | Yuuchi et al. |
| 5,113,859 A | 5/1992 | Funke |
| 5,113,869 A | 5/1992 | Nappholz et al. |
| 5,117,824 A | 6/1992 | Keimel et al. |
| 5,127,401 A | 7/1992 | Grevious et al. |
| 5,133,353 A | 7/1992 | Hauser |
| 5,144,950 A | 9/1992 | Stoop et al. |
| 5,170,784 A | 12/1992 | Ramon et al. |
| 5,179,945 A | 1/1993 | Van Hofwegen et al. |
| 5,193,539 A | 3/1993 | Schulman et al. |
| 5,193,540 A | 3/1993 | Schulman et al. |
| 5,241,961 A | 9/1993 | Henry |
| 5,243,977 A | 9/1993 | Trabucco et al. |
| 5,259,387 A | 11/1993 | dePinto |
| 5,269,326 A | 12/1993 | Verrier |
| 5,284,136 A | 2/1994 | Hauck et al. |
| 5,300,107 A | 4/1994 | Stokes et al. |
| 5,301,677 A | 4/1994 | Hsung |
| 5,305,760 A | 4/1994 | McKown et al. |
| 5,312,439 A | 5/1994 | Loeb |
| 5,313,953 A | 5/1994 | Yomtov et al. |
| 5,314,459 A | 5/1994 | Swanson et al. |
| 5,318,597 A | 6/1994 | Hauck et al. |
| 5,324,316 A | 6/1994 | Schulman et al. |
| 5,331,966 A | 7/1994 | Bennett et al. |
| 5,334,222 A | 8/1994 | Salo et al. |
| 5,342,408 A | 8/1994 | deCoriolis et al. |
| 5,370,667 A | 12/1994 | Alt |
| 5,372,606 A | 12/1994 | Lang et al. |
| 5,376,106 A | 12/1994 | Stahmann et al. |
| 5,383,915 A | 1/1995 | Adams |
| 5,388,578 A | 2/1995 | Yomtov et al. |
| 5,404,877 A | 4/1995 | Nolan et al. |
| 5,405,367 A | 4/1995 | Schulman et al. |
| 5,411,031 A | 5/1995 | Yomtov |
| 5,411,525 A | 5/1995 | Swanson et al. |
| 5,411,535 A | 5/1995 | Fujii et al. |
| 5,456,691 A | 10/1995 | Snell |
| 5,458,622 A | 10/1995 | Alt |
| 5,466,246 A | 11/1995 | Silvian |
| 5,468,254 A | 11/1995 | Hahn et al. |
| 5,472,453 A | 12/1995 | Alt |
| 5,522,866 A | 6/1996 | Fernald |
| 5,540,727 A | 7/1996 | Tockman et al. |
| 5,545,186 A | 8/1996 | Olson et al. |
| 5,545,202 A | 8/1996 | Dahl et al. |
| 5,571,146 A | 11/1996 | Jones et al. |
| 5,591,214 A | 1/1997 | Lu |
| 5,620,466 A | 4/1997 | Haefner et al. |
| 5,634,938 A | 6/1997 | Swanson et al. |
| 5,649,968 A | 7/1997 | Alt et al. |
| 5,662,688 A | 9/1997 | Haefner et al. |
| 5,674,259 A | 10/1997 | Gray |
| 5,683,426 A | 11/1997 | Greenhut et al. |
| 5,683,432 A | 11/1997 | Goedeke et al. |
| 5,702,427 A | 12/1997 | Ecker et al. |
| 5,706,823 A | 1/1998 | Wodlinger |
| 5,709,215 A | 1/1998 | Perttu et al. |
| 5,720,770 A | 2/1998 | Nappholz et al. |
| 5,728,154 A | 3/1998 | Crossett et al. |
| 5,741,314 A | 4/1998 | Daly et al. |
| 5,741,315 A | 4/1998 | Lee et al. |
| 5,752,976 A | 5/1998 | Duffin et al. |
| 5,752,977 A | 5/1998 | Grevious et al. |
| 5,755,736 A | 5/1998 | Gillberg et al. |
| 5,759,199 A | 6/1998 | Snell et al. |
| 5,774,501 A | 6/1998 | Halpern et al. |
| 5,792,195 A | 8/1998 | Carlson et al. |
| 5,792,202 A | 8/1998 | Rueter |
| 5,792,203 A | 8/1998 | Schroeppel |
| 5,792,205 A | 8/1998 | Alt et al. |
| 5,792,208 A | 8/1998 | Gray |
| 5,814,089 A | 9/1998 | Stokes et al. |
| 5,827,216 A | 10/1998 | Igo et al. |
| 5,836,985 A | 11/1998 | Goyal et al. |
| 5,836,987 A | 11/1998 | Baumann et al. |
| 5,842,977 A | 12/1998 | Lesho et al. |
| 5,855,593 A | 1/1999 | Olson et al. |
| 5,873,894 A | 2/1999 | Vandegriff et al. |
| 5,891,184 A | 4/1999 | Lee et al. |
| 5,897,586 A | 4/1999 | Molina |
| 5,899,876 A | 5/1999 | Flower |
| 5,899,928 A | 5/1999 | Sholder et al. |
| 5,919,214 A | 7/1999 | Ciciarelli et al. |
| 5,935,078 A | 8/1999 | Feierbach |
| 5,941,906 A | 8/1999 | Barreras, Sr. et al. |
| 5,944,744 A | 8/1999 | Paul et al. |
| 5,954,757 A | 9/1999 | Gray |
| 5,978,713 A | 11/1999 | Prutchi et al. |

(56) References Cited

U.S. PATENT DOCUMENTS

| | | |
|---|---|---|
| 5,991,660 A | 11/1999 | Goyal |
| 5,991,661 A | 11/1999 | Park et al. |
| 5,999,848 A | 12/1999 | Gord et al. |
| 5,999,857 A | 12/1999 | Weijand et al. |
| 6,016,445 A | 1/2000 | Baura |
| 6,026,320 A | 2/2000 | Carlson et al. |
| 6,029,085 A | 2/2000 | Olson et al. |
| 6,041,250 A | 3/2000 | dePinto |
| 6,044,298 A | 3/2000 | Salo et al. |
| 6,044,300 A | 3/2000 | Gray |
| 6,055,454 A | 4/2000 | Heemels |
| 6,073,050 A | 6/2000 | Griffith |
| 6,076,016 A | 6/2000 | Feierbach |
| 6,077,236 A | 6/2000 | Cunningham |
| 6,080,187 A | 6/2000 | Alt et al. |
| 6,083,248 A | 7/2000 | Thompson |
| 6,106,551 A | 8/2000 | Crossett et al. |
| 6,115,636 A | 9/2000 | Ryan |
| 6,128,526 A | 10/2000 | Stadler et al. |
| 6,141,581 A | 10/2000 | Olson et al. |
| 6,141,588 A | 10/2000 | Cox et al. |
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,505,077 B1 | 1/2003 | Kast et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,575 B2 | 12/2006 | Ostroff et al. |
| 7,149,581 B2 | 12/2006 | Goedeke |
| 7,149,588 B2 | 12/2006 | Lau et al. |

(56) References Cited

U.S. PATENT DOCUMENTS

| | | |
|---|---|---|
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,189,204 B2 | 3/2007 | Ni et al. |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,376,458 B2 | 5/2008 | Palreddy et al. |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,477,935 B2 | 1/2009 | Palreddy et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,340 B2 | 8/2010 | Sanghera et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,809,441 B2 | 10/2010 | Kane et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hubinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |

(56) References Cited

U.S. PATENT DOCUMENTS

| | | |
|---|---|---|
| 7,979,136 B2 | 7/2011 | Young et al. |
| 7,983,753 B2 | 7/2011 | Severin |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,010,209 B2 | 8/2011 | Jacobson |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,080 B2 | 10/2011 | Von Arx et al. |
| 8,050,297 B2 | 11/2011 | DelMain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |
| 8,079,959 B2 | 12/2011 | Sanghera et al. |
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,116,867 B2 | 2/2012 | Ostroff |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,157,813 B2 | 4/2012 | Ko et al. |
| 8,160,672 B2 | 4/2012 | Kim et al. |
| 8,160,700 B1 * | 4/2012 | Ryu .................. A61N 1/3627 607/25 |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,195,308 B2 | 6/2012 | Frank et al. |
| 8,200,341 B2 | 6/2012 | Sanghera et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,034 B2 | 12/2012 | Patangay et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,399 B2 | 7/2013 | Degroot et al. |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,483,843 B2 | 7/2013 | Sanghera et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,878 B2 | 10/2013 | Allavatam et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,626,310 B2 | 1/2014 | Barror et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |

(56) References Cited

U.S. PATENT DOCUMENTS

| | | |
|---|---|---|
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,325 B2 | 11/2014 | Boling et al. |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,072,914 B2 | 7/2015 | Greenhut et al. |
| 9,079,035 B2 | 7/2015 | Sanghera et al. |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,457,193 B2 | 10/2016 | Klimovitch et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 9,511,233 B2 | 12/2016 | Sambelashvili |
| 9,511,236 B2 | 12/2016 | Varady et al. |
| 9,511,237 B2 | 12/2016 | Deterre et al. |
| 9,522,276 B2 | 12/2016 | Shen et al. |
| 9,522,280 B2 | 12/2016 | Fishler et al. |
| 9,526,522 B2 | 12/2016 | Wood et al. |
| 9,526,891 B2 | 12/2016 | Eggen et al. |
| 9,526,909 B2 | 12/2016 | Stahmann et al. |
| 9,533,163 B2 | 1/2017 | Klimovitch et al. |
| 9,561,382 B2 | 2/2017 | Persson et al. |
| 9,566,012 B2 | 2/2017 | Greenhut et al. |
| 9,636,511 B2 | 5/2017 | Carney et al. |
| 9,669,223 B2 | 6/2017 | Auricchio et al. |
| 9,687,654 B2 | 6/2017 | Sheldon et al. |
| 9,687,655 B2 | 6/2017 | Pertijs et al. |
| 9,687,659 B2 | 6/2017 | Von Arx et al. |
| 9,694,186 B2 | 7/2017 | Carney et al. |
| 9,782,594 B2 | 10/2017 | Stahmann et al. |
| 9,782,601 B2 | 10/2017 | Ludwig |
| 9,789,317 B2 | 10/2017 | Greenhut et al. |
| 9,789,319 B2 | 10/2017 | Sambelashvili |
| 9,808,617 B2 | 11/2017 | Ostroff et al. |
| 9,808,628 B2 | 11/2017 | Sheldon et al. |
| 9,808,631 B2 | 11/2017 | Maile et al. |
| 9,808,632 B2 | 11/2017 | Reinke et al. |
| 9,808,633 B2 | 11/2017 | Bonner et al. |
| 9,808,637 B2 | 11/2017 | Sharma et al. |
| 9,855,414 B2 | 1/2018 | Marshall et al. |
| 9,855,430 B2 | 1/2018 | Ghosh et al. |
| 9,855,435 B2 | 1/2018 | Sahabi et al. |
| 9,861,815 B2 | 1/2018 | Tran et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |

(56) References Cited

U.S. PATENT DOCUMENTS

| | | |
|---|---|---|
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0135242 A1* | 7/2003 | Mongeon ............. A61N 1/3956 607/5 |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0275522 A1 | 11/2008 | Dong et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | Brooke |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0264949 A1 | 10/2009 | Dong et al. |
| 2009/0266573 A1 | 10/2009 | Engmark et al. |
| 2009/0270937 A1 | 10/2009 | Yonce et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |

(56) References Cited

U.S. PATENT DOCUMENTS

| | | |
|---|---|---|
| 2010/0063562 A1 | 3/2010 | Cowan et al. |
| 2010/0094367 A1 | 4/2010 | Sen |
| 2010/0094370 A1* | 4/2010 | Levin .................. A61N 1/3621 607/19 |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0305646 A1 | 12/2010 | Schulte et al. |
| 2010/0312309 A1 | 12/2010 | Harding |
| 2010/0331905 A1 | 12/2010 | Li et al. |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0178567 A1 | 7/2011 | Pei et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0029335 A1 | 2/2012 | Sudam et al. |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0185007 A1* | 7/2012 | Ziegler .............. A61N 1/36114 607/11 |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0030484 A1 | 1/2013 | Zhang et al. |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0245709 A1 | 9/2013 | Bohn et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0310890 A1 | 11/2013 | Sweeney |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012344 A1 | 1/2014 | Hastings et al. |
| 2014/0018876 A1 | 1/2014 | Ostroff |

(56) References Cited

U.S. PATENT DOCUMENTS

| | | |
|---|---|---|
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0163631 A1 | 6/2014 | Maskara et al. |
| 2014/0169162 A1 | 6/2014 | Romano et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207013 A1 | 7/2014 | Lian et al. |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222099 A1 | 8/2014 | Sweeney |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0236253 A1 | 8/2014 | Ghosh et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0032173 A1 | 1/2015 | Ghosh |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0142069 A1 | 5/2015 | Sambelashvili |
| 2015/0142070 A1 | 5/2015 | Sambelashvili |
| 2015/0157861 A1 | 6/2015 | Aghassian |
| 2015/0165199 A1 | 6/2015 | Karst et al. |
| 2015/0173655 A1 | 6/2015 | Demmer et al. |
| 2015/0182751 A1 | 7/2015 | Ghosh et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297902 A1 | 10/2015 | Stahmann et al. |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321012 A1 | 11/2015 | Cinbis et al. |
| 2015/0321016 A1 | 11/2015 | O'Brien et al. |
| 2015/0328459 A1 | 11/2015 | Chin et al. |
| 2015/0360036 A1 | 12/2015 | Kane et al. |
| 2016/0007873 A1 | 1/2016 | Huelskamp et al. |
| 2016/0015322 A1 | 1/2016 | Anderson et al. |
| 2016/0023000 A1 | 1/2016 | Cho et al. |
| 2016/0030757 A1 | 2/2016 | Jacobson |
| 2016/0033177 A1 | 2/2016 | Barot et al. |
| 2016/0038742 A1 | 2/2016 | Stahmann et al. |
| 2016/0045131 A1 | 2/2016 | Siejko |
| 2016/0045132 A1 | 2/2016 | Siejko |
| 2016/0045136 A1 | 2/2016 | Siejko et al. |
| 2016/0059007 A1 | 3/2016 | Koop |
| 2016/0059022 A1 | 3/2016 | Stahmann et al. |
| 2016/0059024 A1 | 3/2016 | Stahmann et al. |
| 2016/0059025 A1 | 3/2016 | Stahmann et al. |
| 2016/0089539 A1 | 3/2016 | Gilkerson et al. |
| 2016/0121127 A1 | 5/2016 | Klimovitch et al. |
| 2016/0121128 A1 | 5/2016 | Fishler et al. |
| 2016/0121129 A1 | 5/2016 | Persson et al. |
| 2016/0144190 A1 | 5/2016 | Cao et al. |
| 2016/0151621 A1 | 6/2016 | Maile et al. |
| 2016/0175601 A1 | 6/2016 | Nabutovsky et al. |
| 2016/0206892 A1 | 7/2016 | Demmer |
| 2016/0213919 A1 | 7/2016 | Suwito et al. |
| 2016/0213937 A1 | 7/2016 | Reinke et al. |
| 2016/0213939 A1 | 7/2016 | Carney et al. |
| 2016/0228026 A1 | 8/2016 | Jackson |
| 2016/0250478 A1 | 9/2016 | Greenhut et al. |
| 2016/0271406 A1 | 9/2016 | Maile et al. |
| 2016/0277097 A1 | 9/2016 | Ludwig et al. |
| 2016/0296131 A1 | 10/2016 | An et al. |
| 2016/0317825 A1 | 11/2016 | Jacobson |
| 2016/0367823 A1 | 12/2016 | Cowan et al. |
| 2017/0014629 A1 | 1/2017 | Ghosh et al. |
| 2017/0021159 A1 | 1/2017 | Reddy et al. |
| 2017/0035315 A1 | 2/2017 | Jackson |
| 2017/0043173 A1 | 2/2017 | Sharma et al. |
| 2017/0043174 A1 | 2/2017 | Greenhut et al. |
| 2017/0056665 A1 | 3/2017 | Kane et al. |
| 2017/0056666 A1 | 3/2017 | Kane et al. |
| 2017/0112399 A1 | 4/2017 | Brisben et al. |
| 2017/0113040 A1 | 4/2017 | Brisben et al. |
| 2017/0113050 A1 | 4/2017 | Brisben et al. |
| 2017/0113053 A1 | 4/2017 | Brisben et al. |
| 2017/0156617 A1 | 6/2017 | Allavatam et al. |
| 2017/0189681 A1 | 7/2017 | Anderson |
| 2017/0281261 A1 | 10/2017 | Shuros et al. |
| 2017/0281952 A1 | 10/2017 | Shuros et al. |
| 2017/0281953 A1 | 10/2017 | Min et al. |
| 2017/0281955 A1 | 10/2017 | Maile et al. |
| 2017/0312531 A1 | 11/2017 | Sawchuk |
| 2017/0368360 A1 | 12/2017 | Hahn et al. |
| 2018/0008829 A1 | 1/2018 | An et al. |
| 2018/0008831 A1 | 1/2018 | An et al. |
| 2018/0021567 A1 | 1/2018 | An et al. |
| 2018/0021581 A1 | 1/2018 | An et al. |
| 2018/0021582 A1 | 1/2018 | An et al. |

(56) References Cited

U.S. PATENT DOCUMENTS

| | | |
|---|---|---|
| 2018/0021584 A1 | 1/2018 | An et al. |
| 2018/0036527 A1 | 2/2018 | Reddy et al. |
| 2018/0056075 A1 | 3/2018 | Hahn et al. |
| 2018/0056079 A1 | 3/2018 | Hahn et al. |
| 2018/0078773 A1 | 3/2018 | Thakur et al. |
| 2018/0116593 A1 | 5/2018 | An et al. |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |
| WO | 2016118735 A1 | 7/2016 |

OTHER PUBLICATIONS

International Search Report and Written Opinion dated Jan. 26, 2018 for International Application No. PCT/US2017/060284.

"Instructions for Use System 1, Leadless Cardiac Pacemaker (LCP) and Delivery Catheter," Nanostim Leadless Pacemakers, pp. 1-28, 2013.

Hachisuka et al., "Development and Performance Analysis of an Intra-Body Communication Device," The 12th International Conference on Solid State Sensors, Actuators and Microsystems, vol. 4A1.3, pp. 1722-1725, 2003.

Spickler et al., "Totally Self-Contained Intracardiac Pacemaker," Journal of Electrocardiology, vol. 3(3&4): 324-331, 1970.

Wegmüller, "Intra-Body Communication for Biomedical Sensor Networks," Diss. ETH, No. 17323, 1-173, 2007.

Seyedi et al., "A Survey on Intrabody Communications for Body Area Network Application," IEEE Transactions on Biomedical Engineering, vol. 60(8): 2067-2079, 2013.

* cited by examiner

LCP BASED PREDICTIVE TIMING FOR CARDIAC RESYNCHRONIZATION

CROSS REFERENCE TO RELATED APPLICATIONS

The present application claims the benefit of and priority to U.S. Provisional Patent Application Ser. No. 62/424,582, filed on Nov. 21, 2016, and titled LCP BASED PREDICTIVE TIMING FOR CARDIAC RESYNCHRONIZATION, the disclosure of which is incorporated herein by reference.

BACKGROUND

Cardiac resynchronization therapy (CRT) modifies the electrical activation and contractions of the heart's chambers to enhance pumping efficiency. Benefits may include increased exercise capacity and reduced hospitalization and mortality. More particularly, CRT devices operate by affecting the timing of contraction of one or more cardiac chambers relative to one or more other cardiac chambers. For example, contractions of one or more of the ventricle(s) may be timed relative to contraction of the atria, or contractions of the left and right ventricles may be timed relative to one another.

A "fusion" beat occurs when multiple activation signals affect the same cardiac tissue at the same time. For example, electrical fusion between pacing of one ventricle with spontaneous activation of another ventricle (for example, paced left ventricular (LV) activation and intrinsic right ventricular (RV) activation) produces a fusion beat. The generation of fusion beats is a goal of CRT in many circumstances.

Prior systems generally include intracardiac electrodes coupled via transvenous leads to an implanted pulse generator. The leads of such systems are widely known as introducing various morbidities and are prone to eventual conductor and/or insulator failure. Such issues likely reduce usage of CRT within the indicated population of heart failure patients.

Such prior lead systems typically include ventricular and atrial components to facilitate sensing of atrial and ventricular events to enhance CRT timing. For example, in some patients, CRT may be achieved by pacing the left ventricle at a specific time relative to detection of an atrial event. The sensed atrial signal may conduct to the right ventricle (RV) via natural conduction to generate an RV contraction, with paced LV contraction occurring at a desirable time relative to the RV contraction to yield a fusion beat. The interval from the atrial sensed event to the LV pace may be adjusted to enhance cardiac response in prior systems.

Newer generation pacemakers include the leadless cardiac pacemaker (LCP), which can be implanted entirely within the heart and does not require a transvenous (or any) lead. Such devices are commercially available on a limited basis, but are currently indicated for and capable of use in only bradycardia pacing. With further enhancements, the LCP also presents an opportunity to provide an alternative to traditional CRT using transvenous leads. New and alternative systems, devices and methods directed at providing CRT using the LCP are desired.

OVERVIEW

The present inventor has recognized, among other things, that a problem to be solved is that the absence of an intracardiac lead makes detection of an atrial event for purposes of CRT potentially difficult for a system using one or more ventricular LCP devices. Methods and devices to facilitate CRT from an LCP implanted in the left ventricle are disclosed. These methods may be used in a stand-alone LCP, or in a system comprising both an LCP and one or more additional devices such as another LCP, an implantable cardiac monitor, or an implantable defibrillator.

A first illustrative and non-limiting example takes the form of a method of delivering cardiac resynchronization therapy (CRT) from a leadless cardiac pacemaker (LCP) implanted in or proximate to the left ventricle of a patient, the method comprising: in an initialization phase: determining a PR interval for the patient's cardiac activity; and determining a reduction factor related to at least the PR interval; in a pacing phase, performing the following in iterations: measuring a native beat interval; delivering at least one synchronization pace at an interval that is reduced relative to the native beat interval by the reduction factor; and delivering a plurality, "N", of pacing therapies at a therapy interval; wherein the therapy interval is approximately equal to the native beat interval.

Additionally or alternatively, the LCP may be implanted such that the LCP lacks an atrial lead or electrodes to independently provide timing references from the atria for therapy delivery.

Additionally or alternatively, the step of determining the reduction factor may comprise using an external programmer to receive the reduction factor.

Additionally or alternatively, the step of determining the reduction factor may comprise multiplying the PR interval by a variable, % PR, to determine the reduction factor.

Additionally or alternatively, the variable % PR may be obtained using an external programmer or from a stored value in the LCP.

Additionally or alternatively, the reduction factor may be calculated as follows: in the initialization phase, a ratio of the RR interval between native ventricular events and a PR interval within one or more native ventricular events is calculated and stored as a first variable; a variable, % PR is obtained from memory or from a user/physician; and the reduction factor is calculated as one minus the product of the first variable and the % PR; and further wherein in the pacing phase, the synchronization pace is delivered at an interval calculated by multiplying the reduction factor and native beat interval.

Additionally or alternatively, the PR interval may be obtained in-clinic and entered via an external programmer. Additionally or alternatively, the PR interval is measured by a second implantable medical device monitoring one or more cardiac electrical signals and is then communicated to the LCP.

Additionally or alternatively, the first illustrative method may further comprise: sensing for a patient condition that would influence the reduction factor; detecting a change in the patient condition; and adjusting the reduction factor.

Additionally or alternatively, the first illustrative method may further comprise sensing a posture of the patient; determining that the patient has changed postures; determining that the reduction factor should be adjusted in light of the patient posture change; and adjusting the reduction factor.

Additionally or alternatively, the first illustrative method may further comprise sensing for a patient condition that may influence PR interval, finding that the patient condition has changed, and adjusting "N".

Additionally or alternatively, the first illustrative method may further comprise sensing a posture of the patient; determining that the patient has changed postures between standing and one of sitting or laying down; and: if the patient has gone from standing to sitting or laying down, increasing "N"; or if the patient has gone from sitting or laying down to standing, reducing "N".

A second illustrative and non-limiting example takes the form of a method of delivering cardiac resynchronization therapy (CRT) from a leadless cardiac pacemaker (LCP) implanted in or proximate to the left ventricle of the patient, the method comprising performing a method the first illustrative and non-limiting example (and/or any variant thereof just noted) and further: performing the initialization phase at least once; performing the pacing phase in at least first and second iterations using at least first and second measured native beat intervals; comparing the at least first and second measured native beat intervals and calculating a drift of the native beat interval in the at least first and second iterations; and determining N for use in a subsequent iteration of the pacing phase using the calculated drift.

A third illustrative and non-limiting example takes the form of a method of delivering cardiac resynchronization therapy (CRT) in an implantable medical device system comprising at least a leadless cardiac pacemaker (LCP) and a second implantable medical device, the method comprising: at a first time, delivering CRT in a first CRT method using the LCP to deliver pace therapy and using CRT timing information communicated by the second implantable medical device to control or optimize the CRT; encountering a difficulty with the first CRT method; and switching to performing the method as in the first illustrative and non-limiting example (and/or any variant thereof just noted) or second illustrative example.

A fourth illustrative and non-limiting example takes the form of a leadless cardiac pacemaker (LCP) configured for implantation entirely within a heart chamber of a patient or adjacent to a heart chamber of a patient, the LCP comprising: a plurality of electrodes for therapy delivery and cardiac electrical sensing; pacing circuitry to generate pacing therapy outputs; and control circuitry to control the use of the pacing circuitry using signals sensed from the electrodes; wherein the control circuitry is configured to provide cardiac resynchronization therapy (CRT) in sets using a predetermined reduction factor and a set parameter, "N", comprising delivering sets of CRT therapy including N pacing therapy outputs by: sensing a native R-R interval for the patient's heart; delivering a synchronization pace therapy at an interval, relative to a native ventricular event, calculated using the native R-R interval and the reduction factor; and delivering a plurality of additional pace therapies at intervals approximately equal to the native R-R interval.

Additionally or alternatively, the LCP may be implanted such that the LCP lacks an atrial lead or electrodes to independently provide timing references from the atria for therapy delivery.

Additionally or alternatively, the control circuitry may be configured to provide the CRT without using an atrial sense reference.

Additionally or alternatively, the control circuitry may be configured to perform an initialization of CRT to determine the reduction factor by: determining a PR interval for the patient's cardiac activity; and multiplying the PR interval by a variable, % PR, to calculate the reduction factor.

Additionally or alternatively, the control circuitry may be configured to obtain % PR either by communication with an external programmer or from a stored value in the LCP.

Additionally or alternatively, the control circuitry may be configured to perform an initialization of CRT to determine the reduction factor by: sensing one or more native ventricular events to calculate an RR interval between native ventricular events and a PR interval within one or more native ventricular events; calculating a RR:PR ratio as a ratio of the RR interval to the PR interval; obtaining a variable, % PR, from memory or from an external programmer; and calculating the reduction factor as one minus the product of the first variable and the % PR; and further wherein the control circuitry is configured to calculate the interval for the synchronization pace therapy by multiplying the reduction factor and the native beat interval.

Additionally or alternatively, the control circuitry may be configured to perform an initialization of CRT to determine the reduction factor by: sensing one or more native ventricular events to calculate an RR interval between native ventricular events; communicating with a second device to determine when P-waves occurred in the one or more native ventricular events and calculating a PR interval; calculating a RR:PR ratio as a ratio of the RR interval to the PR interval; obtaining a variable, % PR, from memory or from an external programmer; and calculating the reduction factor as one minus the product of the first variable and the % PR; and further wherein the control circuitry is configured to calculate the interval for the synchronization pace therapy by multiplying the reduction factor and the native beat interval.

Additionally or alternatively, the control circuitry may be configured to monitor patient status and make adjustments to the CRT including: sensing for a patient condition that would influence the reduction factor; detecting a change in the patient condition; and adjusting the reduction factor.

Additionally or alternatively, the LCP may further comprise a posture sensor, wherein the control circuitry may be configured to monitor patient status and make adjustments to the CRT including: sensing a posture of the patient; determining whether the patient has changed postures; and in response to finding that the patient has changed postures, adjusting the reduction factor.

Additionally or alternatively, the control circuitry may be configured to monitor patient status and make adjustments to the CRT including sensing for a predetermined patient condition that may influence PR interval, and in response to sensing the predetermined patient condition, adjusting "N".

Additionally or alternatively, the LCP may further comprise a posture sensor, wherein the control circuitry may be configured to monitor patient status and make adjustments to the CRT including: sensing a posture of the patient; determining that the patient has changed postures between standing and one of sitting or laying down; and: if the patient has gone from standing to sitting or laying down, increasing "N"; or if the patient has gone from sitting or laying down to standing, reducing "N".

Additionally or alternatively, the control circuitry may be configured to iteratively provide the CRT in sets of N pacing pulses and to adjust N after delivery of a plurality of sets of N pacing pulses by: observing changes in native R-R intervals measured prior to delivery of the synchronization pace therapy in the plurality of sets, to calculate an R-R drift; and calculating N using the calculated drift.

Additionally or alternatively, the control circuitry may be configured for at least first and second modes of CRT therapy wherein: the first mode comprises delivering sets of CRT therapy including N pacing therapy outputs via the combination of sensing a native R-R interval, delivering a synchronization pace therapy, and delivering a plurality of additional pace therapies; and the second mode comprises obtaining atrial even timing information from a second implantable or wearable medical device to control or optimize pace therapy timing.

A fifth illustrative and non-limiting example takes the form of an implantable medical device system comprising at least a leadless cardiac pacemaker (LCP) as in the fourth illustrative and non-limiting example (or any of the above variants thereof) and a second implantable medical device, the LCP and the second implantable medical device being configured for communicating with one another, wherein the system is configured to provide cardiac resynchronization therapy (CRT) in at least first and second approaches as follows: the first approach calls for the LCP to perform the first mode; and the second approach calls for the LCP and the second implantable medical device to cooperatively implement the second mode; wherein the system is configured to use the second approach by default and to use the first approach if difficulty is encountered with the second approach.

A sixth illustrative and non-limiting example takes the form of an implantable medical device system comprising at least a leadless cardiac pacemaker (LCP) as in the fourth illustrative and non-limiting example (or any of the above variants thereof) and a second implantable medical device, the LCP and the second implantable medical device being configured for communicating with one another, wherein the system is configured to provide cardiac resynchronization therapy (CRT) in at least first and second approaches as follows: the first approach calls for the LCP to perform the first mode; the second approach calls for the LCP and the second implantable medical device to cooperatively implement the second mode; and wherein the system is configured to use the first approach by default and to use the second approach if difficulty is encountered with the first approach.

An LCP as in any of the fourth, fifth and/or sixth illustrative and non-limiting examples, or any variant thereof, may use a state machine in the control circuitry and/or a microcontroller and memory storing executable instructions for the microcontroller.

This overview is intended to provide an introduction to the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The following description should be read with reference to the drawings. The description and the drawings, which are not necessarily to scale, depict illustrative embodiments and are not intended to limit the scope of the disclosure.

Figure 1:
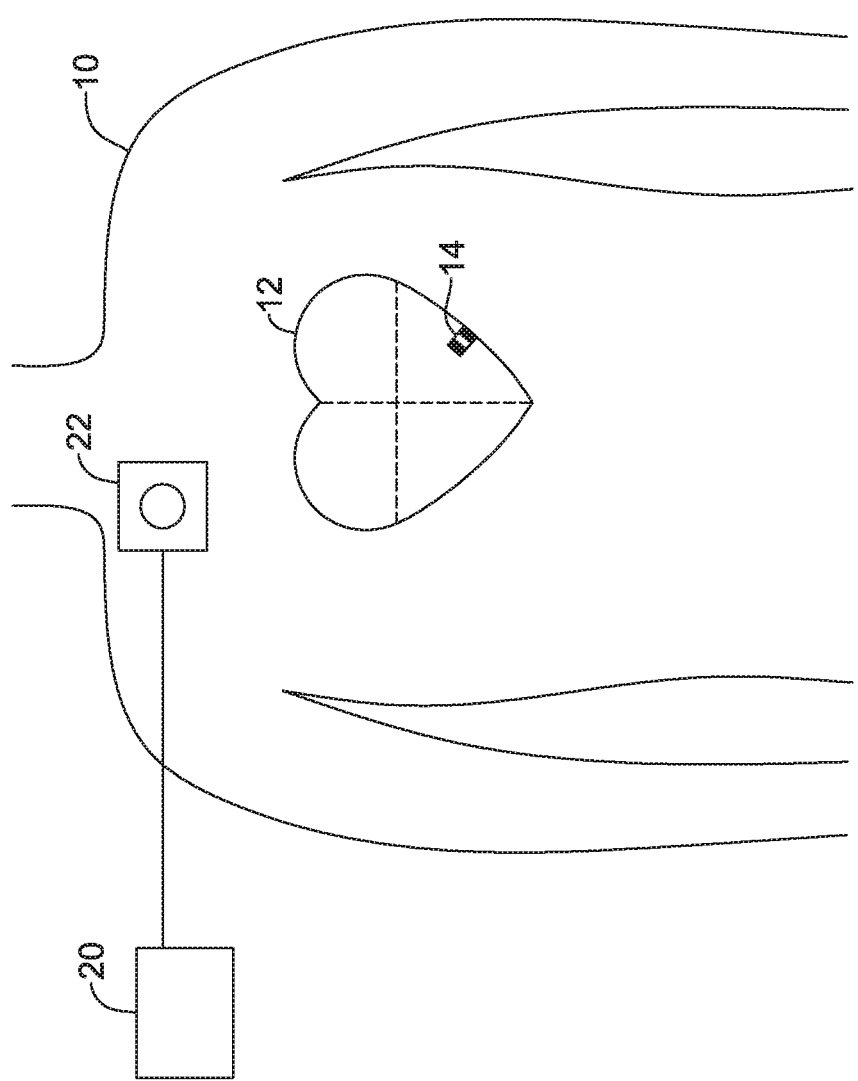
FIG. 1 illustrates a patient having an implanted leadless cardiac pacemaker (LCP) implanted in the left ventricle.

FIG. 1 illustrates a patient 10 having an implanted leadless cardiac pacemaker 14 (LCP placed in the left ventricle of the patient's heart 12. The LCP 14 may be implanted in other chambers, such as the right ventricle, if desired, and as shown below, additional devices may also be implanted to act cooperatively with or independently of the LCP 14. Rather than implantation in the left ventricle, the LCP 14 may be implanted proximate to the left ventricle such as by implantation in a blood vessel of the heart that would place the LCP adjacent to the target chamber.

The LCP 14 is configured for communication with an external device 20 which may be, for example, a clinician programmer or, in some embodiments, may be some other device such as a mobile phone usable by the patient or a remote monitoring apparatus. The external device 20 may perform various processes and methods known in the art such as setting therapy or sensing parameters of the LCP and/or obtaining device diagnostics/settings as well as patient history or other information from the LCP 14.

Communication between the LCP 14 and external device 20 may use an optional wand 22 that can be placed on or near the patient to facilitate communication. For example the wand may be designed with two or more skin contact electrodes for conducted communication with an implantable device. Alternatively the wand may comprise a coil or antenna to facilitate inductive or radiofrequency communications, or may include an optical element(s) for infrared communication, or a transmitter and receiver for ultrasound communications, as desired. For example, Medradio communications in the 401-405 MHz band, Bluetooth or Bluetooth Low Energy, or Zigbee or other communications mode, may be facilitated by the provision of appropriate antennae and associated circuitry. The wand may be omitted and antenna and circuitry may be provided within or on the external device 20. Though not shown in detail, the external device 20 may include any suitable user interface, including a screen, buttons, keyboard, touchscreen, speakers, and various other features widely known in the art.

The LCP 14 may include at least two therapy delivery electrodes to act as anode and cathode for therapy delivery. The LCP 14 may be placed by advancing a catheter into the heart from, for example, a femoral location, and attaining access to the left ventricle and placing the LCP 14 adjacent to the myocardium and engaging attachment features, such as tines, hooks, or helical coils, for example, thereto. Delivery, tissue attachment and retrieval features may be included in the LCP including those features shown in US PG Patent Publications 20150051610, titled LEADLESS CARDIAC PACEMAKER AND RETRIEVAL DEVICE, and 20150025612, titled SYSTEM AND METHODS FOR CHRONIC FIXATION OF MEDICAL DEVICES, the disclosures of which are incorporated herein by reference. Delivery, fixation and retrieval structures may also resemble that of the Micra™ (Medtronic) or Nanostim™ (St. Jude Medical) leadless pacemakers.

The LV placement may be particularly useful for cardiac resynchronization therapy (CRT) purposes. In CRT, as explained in the Background, one goal is to time delivery of pacing to one or more ventricles to cause electrical "fusion" wherein the ventricular contraction is made stronger by activation of tissue due to convergence of multiple electrical signals. A therapy delivered to the LV can converge with the electrical wavefront moving inferiorly through the heart's natural conduction path to enhance cardiac output/efficiency.

While the LV is a good place from which to deliver therapy, an LCP may not be able to adequately sense atrial activity from the LV well enough to independently manage CRT pace timing in all patients and/or at all times. It is likely that in at least some circumstances, an LV-placed LCP will be able to do some atrial sensing using electoral or mechanical signals, however, further options are desired.

Methods described below are intended to provide additional options for an LV located LCP to provide CRT. Such methods may be embodied in devices having operational circuitry configured to perform the methods, such as by including dedicated circuitry for certain functions as well as stored instruction sets to be operated by a processor or controller, or by providing one or more state machines to perform identified functions in various configurations.

Some patients may also or instead need a right ventricle (RV) located LCP to facilitate CRT. The methods and devices herein may be further configured for use in the RV such as by adjusting timing interval calculations to accommodate a location in the RV.

Figure 2:
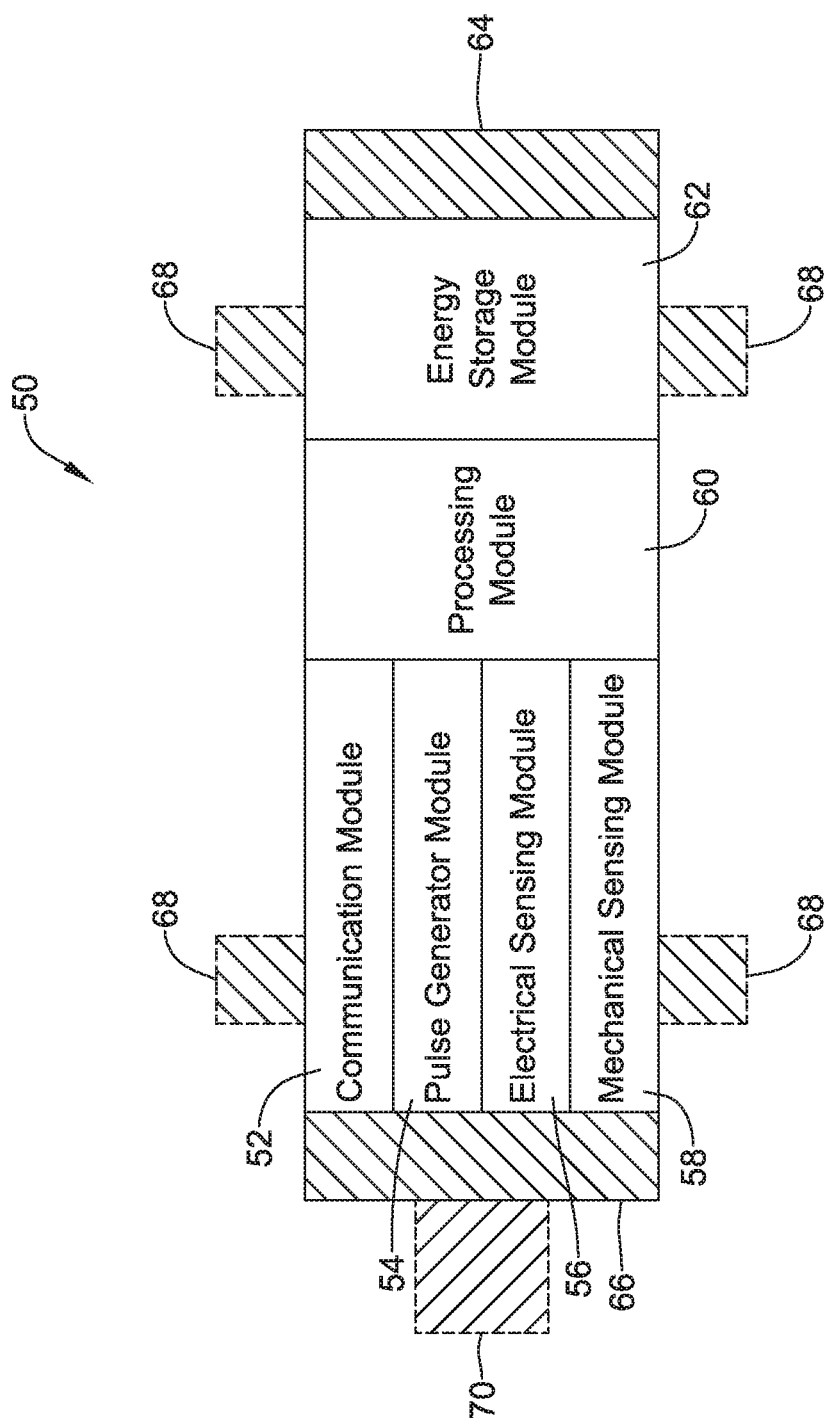
FIG. 2 shows an illustrative implantable leadless cardiac pacemaker.

FIG. 2 shows an illustrative LCP design. The LCP 50 is shown as including several functional blocks including a communications module 52, a pulse generator module 54, an electrical sensing module 56, and a mechanical sensing module 58. In some examples, the electrical sensing module 56 and mechanical sensing module 58 may be configured to sense one or more biological signals for use in one or more of determining timing for CRT, identifying physiological conditions, such as those affecting the parasympathetic nervous system that may affect CRT timing needs, and/or for assessing CRT efficacy, as further described below.

A processing module 60 may receive data from and generate commands for outputs by the other modules 52, 54, 56, 58. An energy storage module is highlighted at 62 and may take the form of a rechargeable or non-rechargeable battery, or a supercapacitor, or any other suitable element. Various details and/or examples of internal circuitry, which may include a microprocessor or a state-machine architecture, are further discussed in US PG Patent Publications 20150360036, titled SYSTEMS AND METHODS FOR RATE RESPONSIVE PACING WITH A LEADLESS CARDIAC PACEMAKER, 20150224320, titled MULTI-CHAMBER LEADLESS PACEMAKER SYSTEM WITH INTER-DEVICE COMMUNICATION, 20160089539, titled REFRACTORY AND BLANKING INTERVALS IN THE CONTEXT OF MULTI-SITE LEFT VENTRICULAR PACING, and 20160059025, titled, MEDICAL DEVICE WITH TRIGGERED BLANKING PERIOD, as well as other patent publications. Illustrative architectures may also resemble those found in the Micra™ (Medtronic) or Nanostim™ (St. Jude Medical) leadless pacemakers.

The device is shown with a first end electrode at 64 and a second end electrode at 66. A retrieval feature is shown schematically at 70 and may be, for example, a short post with an opening therethrough to receive a retrieval hook. A number of tines 68 may extend from the device in several directions. The tines 68 may be used to secure the device in place within a heart chamber. An attachment structure may instead take the form of a helical screw, if desired. In some examples, tines 68 are used as the only attachment features. As noted above, delivery, tissue attachment and retrieval features may be included in the LCP including those features shown in US PG Patent Publications 20150051610, and/or 20150025612, titled SYSTEM AND METHODS FOR CHRONIC FIXATION OF MEDICAL DEVICES, for example. Delivery, fixation and retrieval structures may also resemble that of the Micra™ (Medtronic) or Nanostim™ (St. Jude Medical) leadless pacemakers.

Figure 3:
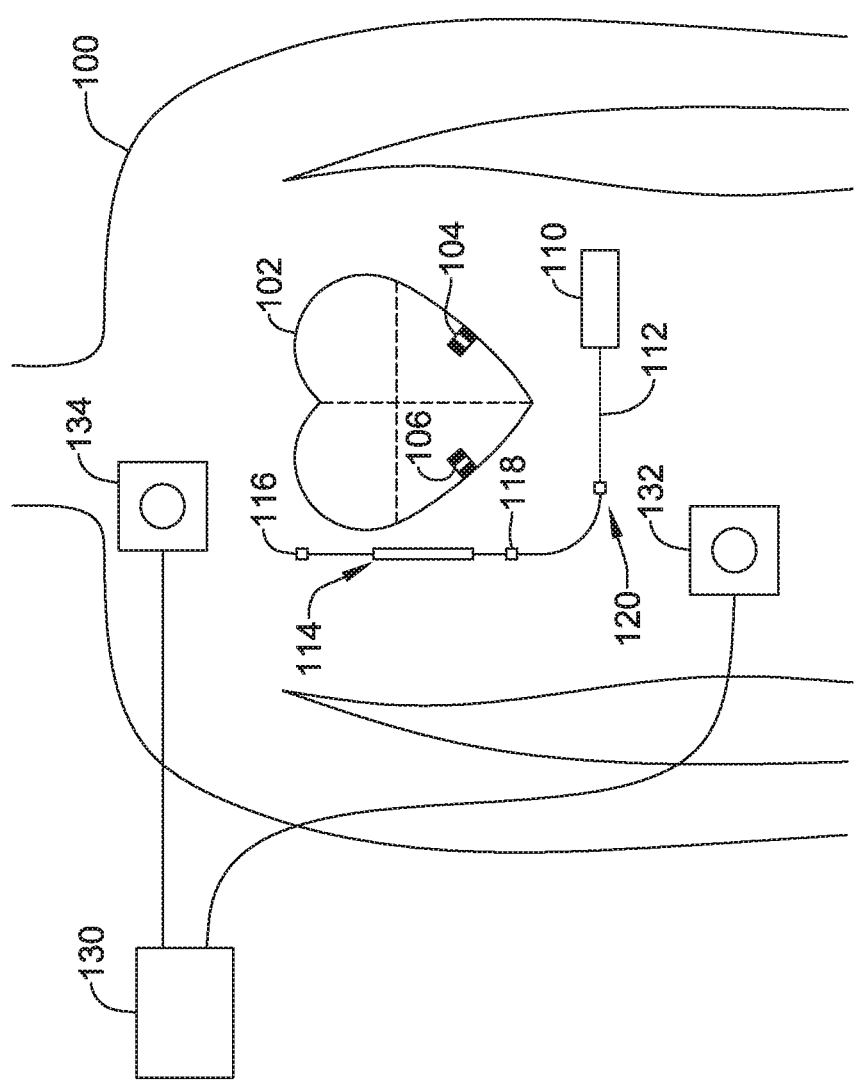
FIG. 3 shows a patient having a plurality of implantable medical devices.

FIG. 3 illustrates a patient 100 with an LCP 104 implanted inside the heart 102, in the left ventricle for illustrative purposes. Optionally a second LCP 106 is shown in the right ventricle of the heart 102. If desired further devices may be provided by having, for example, an LCP in one of the atria.

The patient 100 also has implanted another medical device in the form of a subcutaneous implantable defibrillator (SICD) having a left axillary canister 110 and a lead 112. The illustrative lead 112 is shown with a defibrillation coil 114 and sensing electrodes 116, 118 distal and proximal of the coil 114. A still more proximal sense electrode may also be provided as shown at 120. For securing the lead subcutaneously, one or more suture sleeves may be provided and/or the distal tip electrode 116 may be secured to the fascia by the use of a suture or clip engaging a suture hole in the distal tip.

In some embodiments the lead may be as shown, for example, in U.S. Pat. No. 9,079,035, titled ELECTRODE SPACING IN A SUBCUTANEOUS IMPLANTABLE CARDIAC STIMULUS DEVICE, the disclosure of which is incorporated herein by reference. Plural leads may be provided as shown, for example, in U.S. Pat. No. 7,149,575, titled SUBCUTANEOUS CARDIAC STIMULATOR DEVICE HAVING AN ANTERIORLY POSITIONED ELECTRODE or, alternatively, the lead may have a bifurcation. Any suitable design for single, multiple, or bifurcated implantable leads may be used.

The lead 112 may be implanted entirely subcutaneously, such as by extending across the anterior or posterior of the chest, or by going partly across the chest in a lateral/medial direction and then superiorly toward the head along the sternum. Some examples and discussion of subcutaneous lead implantation may be found in U.S. Pat. No. 8,157,813, titled APPARATUS AND METHOD FOR SUBCUTANEOUS ELECTRODE INSERTION, and US PG Publication No. 20120029335, titled SUBCUTANEOUS LEADS AND METHODS OF IMPLANT AND EXPLANT, the disclosures of which are incorporated herein by reference. Additional subcutaneous placements are discussed in U.S. Pat. No. 6,721,597, titled SUBCUTANEOUS ONLY IMPLANTABLE CARDIOVERTER DEFIBRILLATOR AND OPTIONAL PACER, and the above mentioned U.S. Pat. No. 7,149,575, the disclosures of which are incorporated herein by reference.

A substernal placement may be used instead, with the distal end of the lead 112 (that is, the end distant from the canister 110) going beneath the sternum. Some examples of such placement are described in US PG Patent Pub. No. 20170021159, titled SUBSTERNAL PLACEMENT OF A PACING OR DEFIBRILLATING ELECTRODE, the disclosure of which is incorporated herein by reference. Still another alternative placement is shown in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference.

The devices 104, 106 (optionally), 110 may communicate with one another and/or with an external programmer 130 using conducted communication, in some examples. Conducted communication is communication via electrical signals which propagate via patient tissue and are generated by more or less ordinary electrodes. By using the existing electrodes of the implantable devices, conducted communication does not rely on an antenna and an oscillator/resonant circuit having a tuned center frequency or frequencies common to both transmitter and receiver radiofrequency or inductive communication may be used instead. Alternatively the devices 104, 106 (optionally), 110 may communicate via inductive, optical, sonic, or radiofrequency communication, or any other suitable medium.

Subcutaneous implantable defibrillators may include, for example, the Emblem S-ICD System™ offered by Boston Scientific Corporation. Combinations of subcutaneous defibrillators and LCP devices are discussed, for example, in US PG Patent Publication Nos. 20160059025, 20160059024, 20160059022, 20160059007, 20160038742, 20150297902, 20150196769, 20150196758, 20150196757, and 20150196756, the disclosures of which are incorporated herein by reference. The subcutaneous defibrillator and LCP may, for example, exchange data related to cardiac function or device status, and may operate together as a system to ensure appropriate determination of cardiac condition (such as whether or not a ventricular tachyarrhythmia is occurring), as well as to coordinate therapy such as by having the LCP deliver antitachycardia pacing in an attempt to convert certain arrhythmias before the subcutaneous defibrillator delivers a defibrillation shock. In addition, the two systems may coordinate as set forth herein to provide cardiac resynchronization therapy (CRT).

In some examples, rather than a therapy device such as the SICD shown in FIG. 3, a second implantable medical device may take the form of an implantable monitoring device such as a subcutaneous cardiac monitor (SCM). An SCM may be, for example, a loop monitor that captures data under select conditions using two or more sensing electrodes on a housing thereof and/or attached thereto with a lead. Such monitors have found use to assist in diagnosing cardiac conditions that may be infrequent or intermittent, or which have non-specific symptoms. In the context of the present invention, an SCM, or even a wearable cardiac monitor, may be used in place of the SICD as described in any of the following examples.

Several examples focus on using a left ventricular LCP 104. However, some examples may instead use a right ventricular LCP 106, and other examples may include both the left ventricular LCP 104 and right ventricular LCP 106. In other examples, a three implant system may include two LCP devices 104, 106, as well as a subcutaneous device such as the SICD 110 as shown. In still other examples, an atrial-placed LCP (not shown) may also be included or may take the place of one of the ventricular LCP devices 104, 106 and/or the SICD 110.

Figure 4:
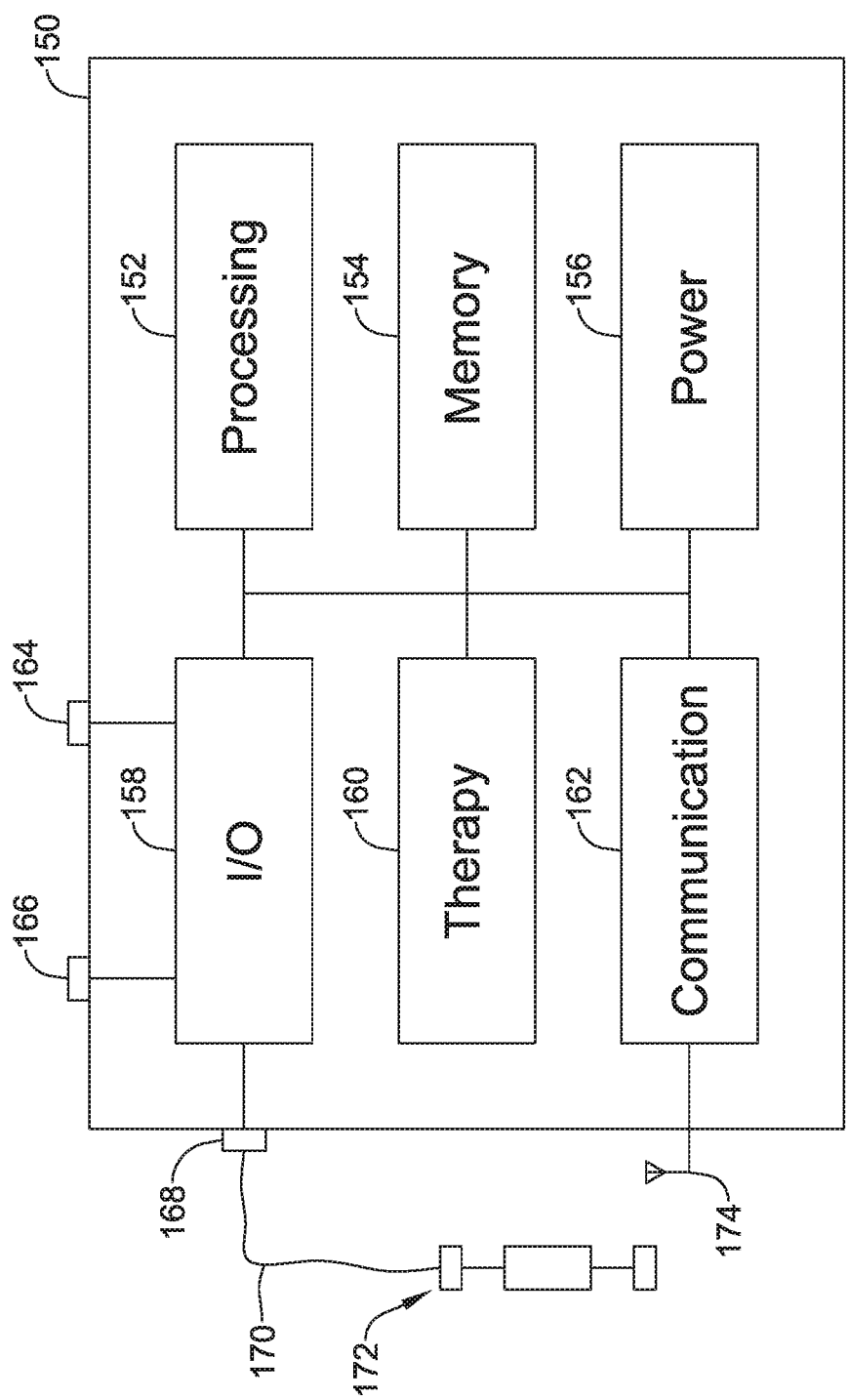
FIG. 4 shows an illustrative implantable medical device.

FIG. 4 illustrates a block diagram of an implantable medical device. The illustration indicates various functional blocks within a device 150, including a processing block 152, memory 154, power supply 156, input/output circuitry 158, therapy circuitry 160, and communication circuitry 162. These functional blocks make up at least some of the operational circuitry of the device. The I/O circuitry 158 can be coupled to one or more electrodes 164, 166 on the housing of the device 150, and may also couple via a header 168 for attachment to one or more leads 170 having additional electrodes 172.

The processing block 152 will generally control operations in the device 150 and may include a microprocessor or microcontroller and/or other circuitry and logic suitable to its purpose. A state machine may be included. Processing block 152 may include dedicated circuits or logic for device functions such as converting analog signals to digital data, processing digital signals, detecting events in a biological signal, etc. The memory block may include RAM, ROM, flash and/or other memory circuits for storing device parameters, programming code, and data related to the use, status, and history of the device 150. The power supply 156 typically includes one to several batteries, which may or may not be rechargeable depending on the device 150. For rechargeable systems there would additionally be charging circuitry for the battery (not shown) including for example a coil for receiving energy and regulating and rectification circuitry to provide received energy to a rechargeable battery or supercapacitor.

The I/O circuitry 158 may include various switches or multiplexors for selecting inputs and outputs for use. I/O circuitry 158 may also include filtering circuitry and amplifiers for pre-processing input signals. In some applications the I/O circuitry will include an H-Bridge to facilitate high power outputs, though other circuit designs may also be used. Therapy block 160 may include capacitors and charging circuits, modulators, and frequency generators for providing electrical outputs. A monitoring device may omit the therapy block 160 and may have a simplified I/O circuitry used simply to capture electrical or other signals such as chemical or motion signals.

The communication circuitry 162 may be coupled to an antenna 174 for radio communication (such as Medradio, ISM, Bluetooth, or other radiofrequency protocol/band), or alternatively to a coil for inductive communication, and/or may couple via the I/O circuitry 158 to a combination of electrodes 164, 166, 172, for conducted communication. Communication circuitry 162 may include a frequency generator/oscillator and mixer for creating output signals to transmit via the antenna 174. Some devices 150 may include a separate or even off-the shelf ASIC for the communications circuitry 162, for example. For devices using an inductive communication output, an inductive coil may be included. Devices may use optical or acoustic communication, and suitable circuits, transducers, generators and receivers may be included for these modes of communication as well or instead of those discussed above.

As those skilled in the art will understand, additional circuits may be provided beyond those shown in FIG. 4. For example, some devices 150 may include a Reed switch, Hall Effect device, or other magnetically reactive element to facilitate magnet wakeup, reset, or therapy inhibition of the device by a user, or to enable an MRI protection mode. A device lacking a lead may have plural electrodes on the housing thereof, as indicated at 164, 166, but may omit the header 168 for coupling to lead 170.

A device as in FIG. 4 may be embodied as a subcutaneous implantable defibrillator as shown above in FIG. 3. Alternatively a device 150 may be embodied as an implantable defibrillator and/or pacemaker as in US PG Patent Pub. No. 20170021159, titled SUBSTERNAL PLACEMENT OF A PACING OR DEFIBRILLATING ELECTRODE, the disclosure of which is incorporated herein by reference. Still another alternative placement is shown in U.S. patent application Ser. No. 15/667,167, titled IMPLANTATION OF AN ACTIVE MEDICAL DEVICE USING THE INTERNAL THORACIC VASCULATURE, the disclosure of which is incorporated herein by reference. Still further, a device 150, omitting the therapy circuitry 160 if desired, may be embodied as an implantable cardiac monitoring system.

Figure 5:
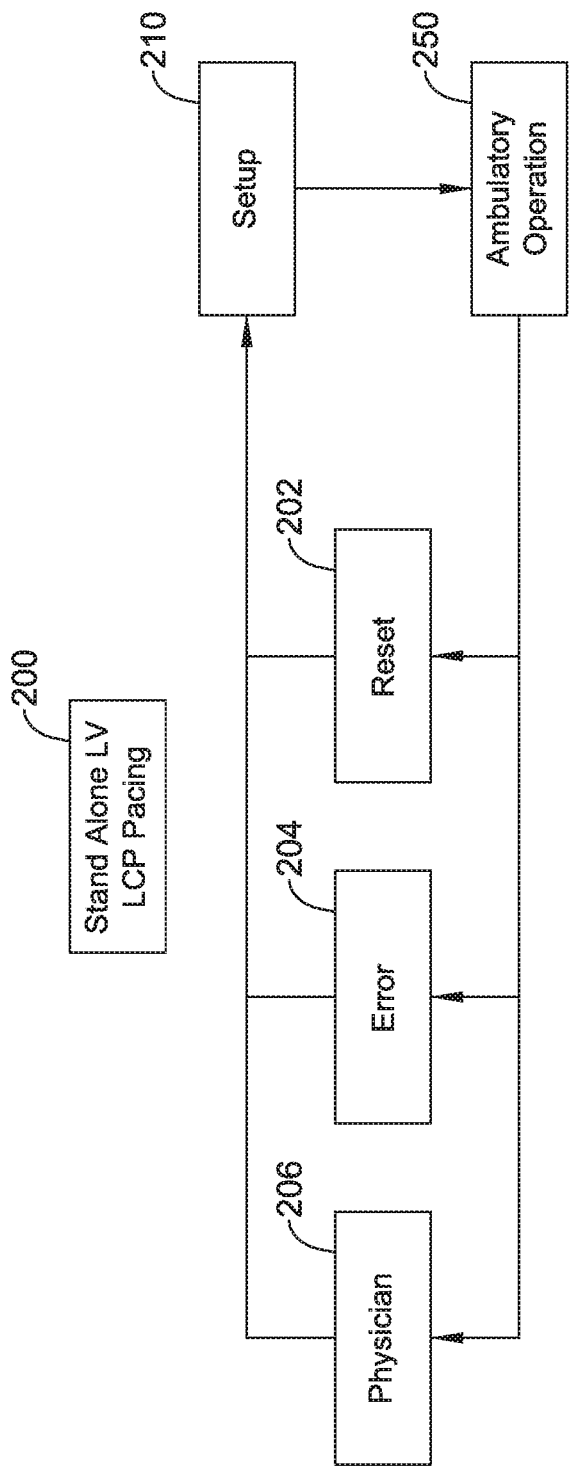
FIGS. 5-7 illustrate a method of LCP pacing for CRT.
Figure 6:
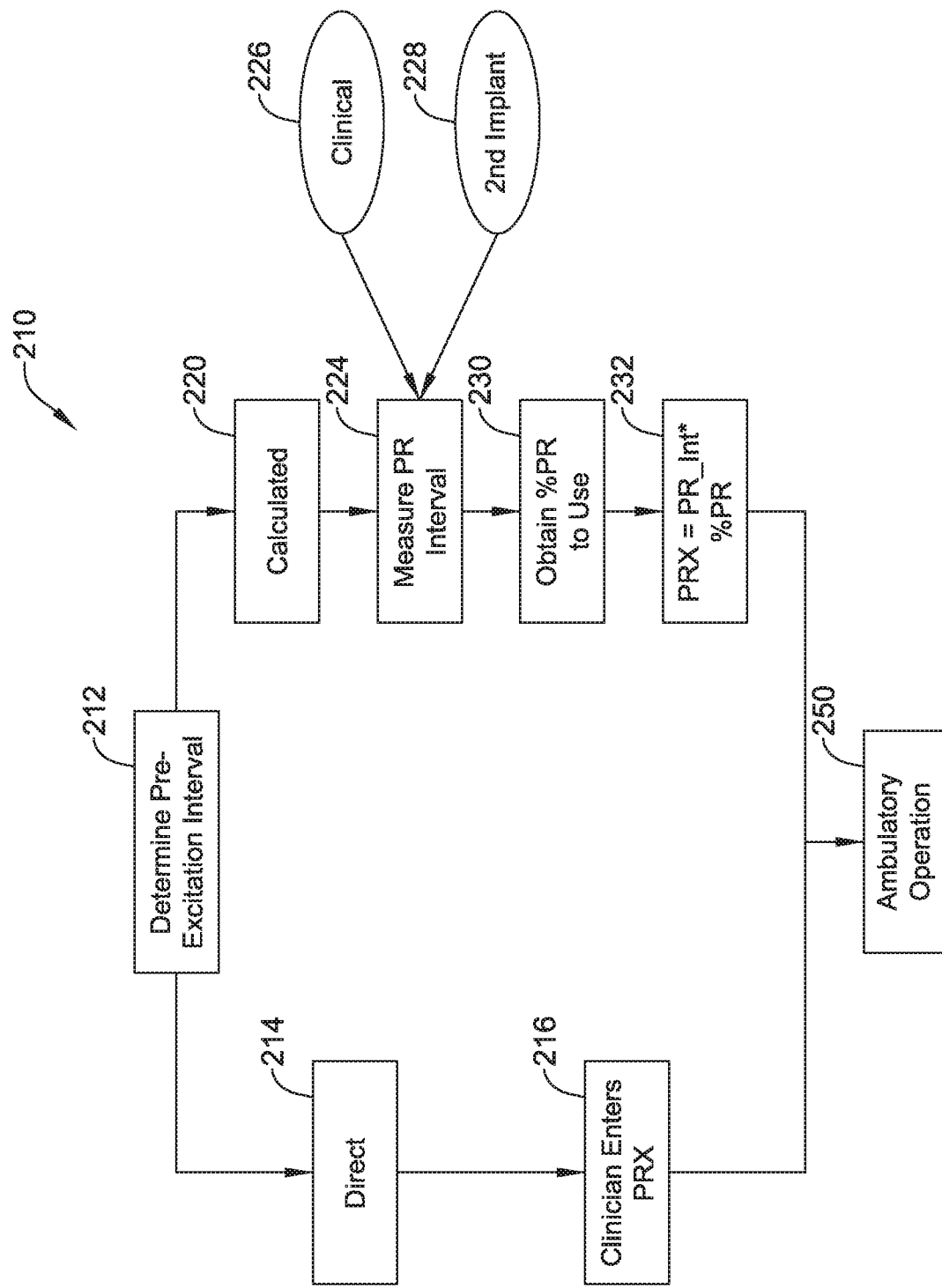
Figure 7:
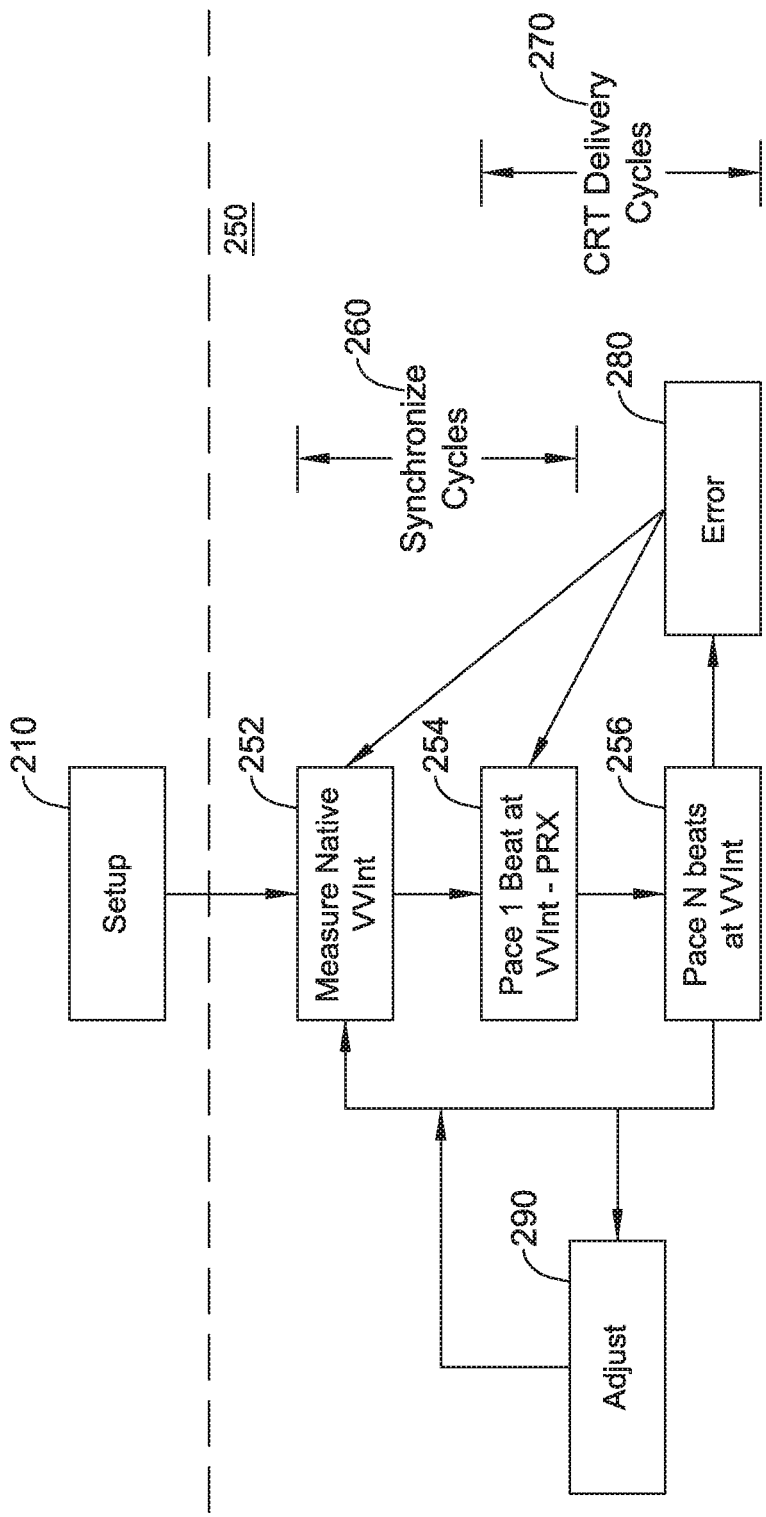

FIGS. 5-7 illustrate a method of LCP pacing for CRT. FIG. 5 shows the method at a high level as being an approach for stand-alone LV LCP pacing, as indicated at 200. A setup process, shown in FIG. 6, is performed as indicated at 210. Next, ambulatory operation 250 takes place, as further detailed below in FIG. 7. Upon occurrence of a reset 202 of the device, optionally, the system may return to the setup process 210. Upon occurrence of one or a plurality of errors, such as a persistent failure of one or more types, setup 210 may be revisited. For example, if desired, one or more measures of CRT success may be monitored such as review of cardiac contractility, occurrence of fusion pacing events, changes in patient fluid status, occurrence of desirable hemodynamic outcomes as indicated by strength of cardiac beats or changes in pressure in the heart or blood vessels, for example, and failure to attain desired outcomes may be viewed as an error 204 triggering return to setup. In the most likely to occur of these return states, a physician intervention may occur, such as when a patient goes to the clinic for a follow-up (or has, if enabled, a follow-up via remote telemetry) with a physician 206 who may oversee a re-visit to the setup 210.

Turning to FIG. 6, the setup process is shown at 210. A pre-excitation interval, PRX, is to be determined as indicated at 212. In a simplest approach, PRX can be directly determined 214 by having the physician enter the desired PRX 216 using a clinician programmer. The entered value for PRX can then be used in ambulatory operation 250 which is further discussed in FIG. 7. PRX is one type of "reduction factor (RF)" that may be used in some embodiments; another example of an RF is also described below.

A calculated approach 220 is also provided. Here, the PR interval is measured 224—that is, an interval from the P-wave to the R-wave for the patient is determined using, for example, measurement of such an interval in one or a plurality of cardiac cycles. Step 224 may be performed in-clinic 226 under the supervision of a physician or otherwise qualified personnel. Alternatively, step 224 may be performed by a second implant 228 such as an extracardiac device (ED), for example, a subcutaneous implantable cardioverter defibrillator (SICD) or subcutaneous cardiac monitor (SCM), or even another LCP. In a still further alternative, the LCP itself may measure a PR interval by, for example, obtaining a heart sound associated with occurrence of a P-wave and assuming an interval between occurrence of the heart sound and the desired atrial fiducial.

Next, a variable, % PR, is obtained for use in calculating PRX, as indicated at 230. The variable may be provided by a physician overseeing the procedure, or it may be pre-set, for example, as a desired target based on general population studies. For example, given a P-R interval, the point in time at which pacing for CRT should be delivered may be assumed to be some fraction of the P-R interval such as in the range of about 25% to about 60%, or about 35% to about 50% of the P-R interval prior to the oncoming R-wave. Thus, as an example, if the RR interval is 1000 ms, the % PR is 60%, and the PR interval is 160 ms, then a pace therapy for CRT may desirably precede the R-wave by 96 ms, or 60% of the PR interval. In the illustrative example, 40% of the PR interval would be subtracted from the RR interval to yield a synchronization pulse interval.

The pre-excitation interval, PRX can then be calculated as the product of the measured PR interval times the obtained or entered % PR, as shown at 232. With PRX calculated, the method then turns to ambulatory operation 250 shown in FIG. 7.

FIG. 7 illustrates steps for ambulatory operation. Following setup 210, a native interval between R-waves, QRS complexes, or "beats" is measured, as indicated at 252.

This interval may be obtained using any suitable method such as by monitoring the electrocardiogram as received at the LCP; other methods may be used such as by monitoring for heart sounds, motion, or pressure events inside the heart, if desired. The interval is "native" insofar as at least the latter cardiac cycle of the two surrounding the interval is not artificially paced. The measured interval is then an interval between two ventricular events, or VVInt. If desired, both of the preceding and following ventricular events defining the native interval may be non-paced.

A single, "Synchronization" occurs with a pace therapy delivered at an interval that is equal to VVInt less PRX, as indicated at 254. Then a plurality of beats are paced at intervals equal to VVInt. By pacing at an interval, as used herein, the intent is that a pace therapy output is delivered following expiration of the interval from a preceding sensed ventricular event or pace therapy delivery. Thus, the pace at 254 follows expiration of an interval following a native ventricular event, while the paces at 256 are each taking place following expiration of an interval following a previous pace therapy delivery.

After "N" beats are paced, the method returns from block 256 to block 252 to obtain a new VVInt. The loop back to measure VVInt acknowledges, in part, that the patient's native heart rate may change over time as, for example and without limitation, the patient moves, undertakes an activity, becomes excited, falls asleep, or is affected by an ingested chemical such as caffeine. In the figure, the combination of blocks 252, 254 serve as synchronization cycles comprising a native cardiac cycle and a paced cardiac cycle. The pace therapy at 254 also serves as a CRT delivery cycle along with those delivered in block 256.

During therapy cycling, the device monitors the cardiac electrical signal to ensure that a new ventricular beat does not occur between pace therapy outputs. Such beats may take place if, for example, an ectopic beat, such as premature ventricular contraction, occurs, or if an atrial arrhythmia such as atrial fibrillation, conducts to the ventricle(s). If this occurs it may be treated as an error as indicated at 280, and may be handled as shown below in FIG. 15, returning to one of block 252 or block 254, as desired. In addition, one or more physiological signals of the patient may be monitored as illustrated below in FIGS. 9-13, yielding an adjustment to one or more parameters as indicated at 290. For example, PRX (or other reduction factor, RF) or "N" may be modified in light of a sensed condition as shown in FIGS. 9-13.

Figure 8A:
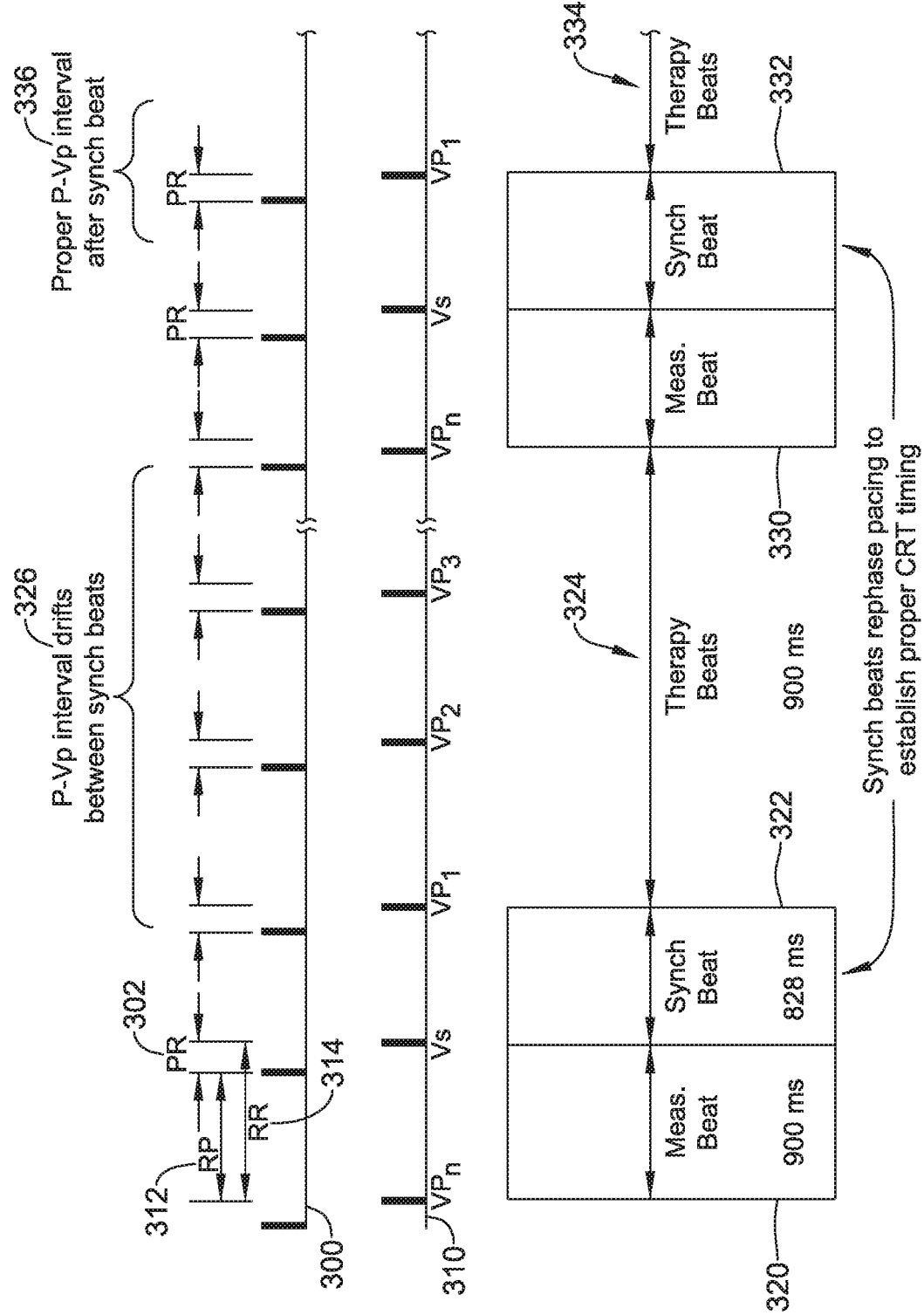
FIG. 8A is a timing diagram illustrating a method as in FIG. 7.

In operation, the method as shown in FIG. 7 will provide a percent therapy delivery for CRT pacing of (N+1)/(N+2). The percent therapy delivery can be manipulated by increasing or decreasing N, and may be further reduced if desired by introducing delays between sets. Studies have shown, however that a higher percent therapy delivery tends to result in greater therapy benefit. On the other hand, as shown in FIG. 8A, the underlying rhythm may drift over time to yield changes in the PR interval and/or RR interval that can reduce efficacy during performance of step 256. These tradeoffs can be handled to some extend by using methods shown in FIGS. 9-13 below to increase or decrease the percent therapy delivery in response to select conditions. In general, a range of N may be anywhere from 5 up to about 50, or higher or lower, if desired. In an example, N may be incremented up and down in steps of 1, 2, 5 or 10, or other increment.

FIG. 8A is a timing diagram illustrating a method as in FIG. 7. Atrial events (P-waves) are shown on the line at 300; each dark vertical line along the horizontal axis at 300 represents a P-wave or atrial depolarization. Axis 310 shows ventricular depolarizations in the dark vertical lines on the horizontal axis. Paced ventricular events on axis 310 are marked as Vp, and native events marked as Vs. Certain intervals are marked for the first two cardiac cycles on the left hand side, including the PR interval at 302 from an atrial event to the subsequent ventricular event, an RP interval at 312 from a ventricular event to the subsequent atrial event, and the RR interval between two consecutive ventricular events at 314. Going to the right hand side of the figure, the PR intervals continue to be called out.

The lower portion of FIG. 8A shows pace intervals with characterizations and durations. At 320 is a measurement beat. The measurement beat is what would be observed at block 252 of FIG. 7, as the ventricular event Vs that ends the interval is a native beat and is not paced. Next a synchronization beat is delivered, as indicated at 322, which would match therapy delivery at block 254 of FIG. 7. Then a set of "N" therapy beats are delivered at 324, corresponding to the delivery of CRT therapy in block 256 of FIG. 7. The process then iterates with a measurement beat at 330, a synch beat at 332, and another set of therapy beats at 334.

Illustrative intervals are shown in blocks 320, 322 and associated with 324. In this example, the measured beat interval has a duration of 900 milliseconds, which would correspond to about 67 beats per minute. The synchronization beat in this example is delivered at a shorter interval, in this case, 828 milliseconds following the native ventricular event Vs that ends the measurement beat interval. For this illustrative, non-limiting example, the value for PRX is 72 milliseconds, which could be calculated, for example, using 45% of a 160 millisecond PR interval. The numerical solution is hypothetical but likely in the range of what a real world patient would experience. Another illustrative approach may take into account the relative length of the PR interval to the RR interval as follows. In an example, the setup phase may determine the RR interval and PR interval at a given point in time and generate a PR:RR ratio. For example, if the RR interval is measured at 800 milliseconds and the PR interval is 160 milliseconds, then the PR:RR interval would be 160/800=0.2, which can be referred to as the "Ratio". Then a Pre-Excitation Percentage (PEP) may be provided by the physician or pre-set by the device, for example in the range of 30% to 50%; in one example, the PEP is set to 40%. In the ambulatory setting, the synchronization pace interval can be set as follows:

Synch_Interval=VVInt*(1−Ratio*PEP)

Assuming VVInt is measured at 900 millisecond, then the outcome given a Ratio of 0.2 and a PEP of 40% is:

Synch_Interval=900 ms*(1−0.2*0.4)=900*(0.92)=828 ms

In operation, for the Ambulatory Setting, block 328 may be revised to state that a pace therapy is delivered at VVInt*Synch_Fraction, where Sync Fraction is the product of the ratio of the measured PR to RR intervals, and the PEP. In the remaining explanation and Figures, PRX and/or the combination calculated factor (1−Ratio*PEP) may be treated as reduction factors (RF) that are used to reduce VVInt for purposes of delivering the Synch Interval.

One of the reasons for limiting "N" is illustrated at 326, where the P to Vp interval drifts as the set of pace therapies are delivered. Drift would again occur within the therapy set at 334; at least for the initial few beats the drift is likely to be small but it may grow over time as device settings and assumptions become less connected to the patient's changing physiological experience.

Such drift is not harmful within reasonable limits. For example, typically, a tolerance for drift may be in the range of 20 milliseconds or so in either direction and so random variation is likely tolerable. However, drift of the P-Vp interval may not be purely random, for example, physiological conditions of the patient can cause drift to occur in a directional manner. For example, if the patient begins exercising or changes posture causing a change in sympathetic tone, the actual underlying PR interval may change, or the patient's heart rate may change causing changes in the RR interval which, in turn would make the pace therapy delivery mis-timed relative to the P-wave as metabolic demand may change the time of P-wave appearing on the atrial axis 300 (which is not paced), but the pacing on the ventricular axis 310 remains fixed. In some examples, also laid out below, the actual PR interval even at the same RR interval may be different depending on certain factors such as posture, and accommodations for that may also be made.

In some examples, N may be selected for a given patient in view of a physician's experience with the patient and/or in light of information gathered for a patient. For example, a patient may receive a wearable monitoring system or implantable monitor to determine PR variability in order to determine how N may be set, in advance of LCP implantation by seeing how quickly the patient's heart rate or other characteristics change in response to activity, posture change, sleep, excitement, etc. In another example, wearable or additional implantable device may be provided after implantation of the LCP to monitor pacing effectiveness for a time period to determine a range for N, as well as other suitable patient diagnostics.

Figure 8B:
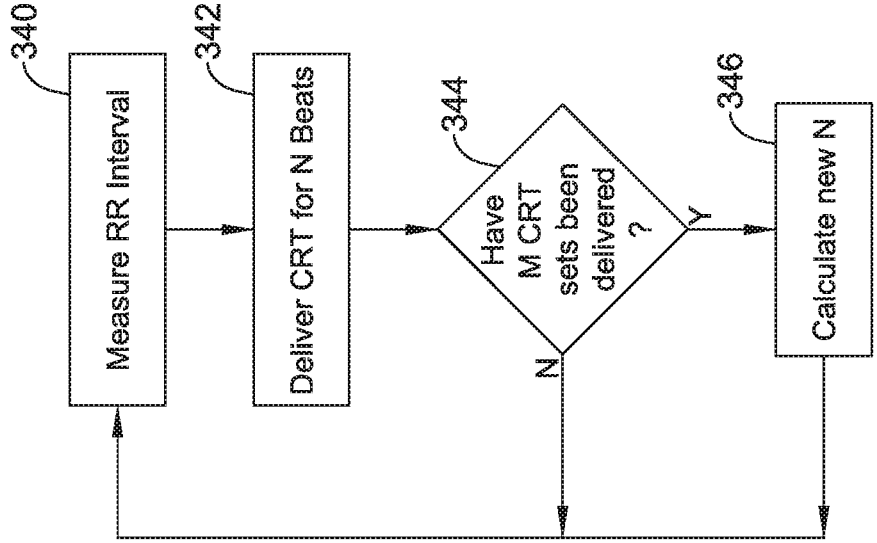
FIG. 8B is a block diagram for overall management of a method of LCP pacing for CRT referencing the timing diagram of FIG. 8A.

FIG. 8B illustrates an example wherein the LCP adjusts N based on the RR interval drift measured by the LCP in prior therapy sets. At 340 the LCP measures the RR interval, for example during the measurement beat 320 (FIG. 8A). At 342 the LCP delivers a set of N beats of CRT as illustrated in FIG. 8A. If at 344, M (e.g. 10) CRT sets have been delivered, a new N is calculated at 346.

In most patients there is a strong relationship between the RR and PR intervals. Thus measuring the RR interval drift ($RR_{Drift}$) can be used to estimate the drift in the PR interval. For example, the PR drift may be about one fifth the RR drift. As noted above, in some examples, the usable value of N is dependent on the PR drift and the tolerance of CRT to deviations from the desired AV delay ($AVD_{Tol}$). In an example, the new N can be calculated as follows:

$$N_{New}=N_{Old}*(5*|AVD_{Tol}/RR_{Drift}|)$$

For example, if over the last 10 CRT sets the RR interval drift is +120 ms, the AV delay tolerance is 30 ms and the present N is 25, the new N would be 25*(5*|30 ms/120 ms|)=31 ($N_{New}$ being rounded to the nearest integer). In another example, if over the last 10 CRT sets the RR interval drift is −150 ms, the AV delay tolerance is 25 ms and the present N is 30, the new N would be 30*(5*|25 ms/−150 ms|)=25. In some examples the ratio of the PR interval to RR interval is fixed (e.g. 5). In some examples the PR interval varies by patient or time and can be attained via physician entry or measurement via another device.

In still other examples, below, N maybe modified in light of additional patient conditions.

Figure 9:
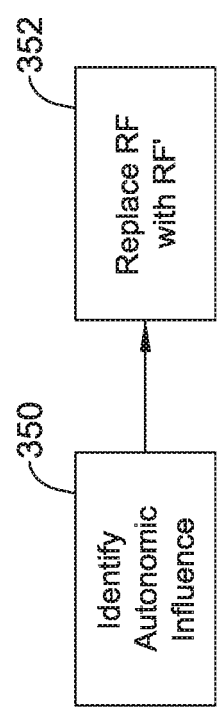
FIGS. 9-13 illustrate sub-methods to adjust a method of LCP pacing for CRT.

FIGS. 9-13 illustrate sub-methods to adjust a method of LCP pacing for CRT. FIG. 9 shows an example in which an adjustment may be made between sets of CRT. In this example, the device (the LCP itself, or a second device communicatively linked to an LCP) identifies a physiological change that likely has an autonomic influence at 350, particularly with focus on any change that may affect the reduction factor (RF). If such a change is observed, a substitute reduction factor is inserted, RF', as indicated at 352. For example, referring to FIG. 7, this type of adjustment may be made at block 290, between therapy sets, as the modification of RF would be of most importance when RF is actually used during the synchronization pace step, and would have less importance, if any, during the actual set of therapies. However, in another example, if desired, the postural change may be used to interrupt the set of CRT pace therapies prior to reaching "N" therapies to force re-synchronization. Such an interruption may be treated as an error 280 forcing a return to the sense or synchronization steps of FIG. 7.

Figure 10:
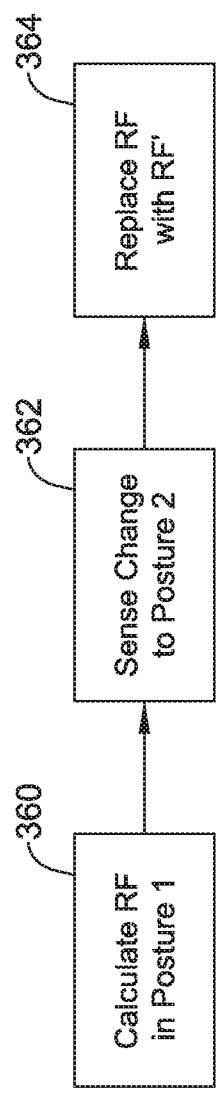

FIG. 10 shows a more specific example of the concept of FIG. 9. Here, RF may be calculated with the patient in a known posture, Posture 1, as indicated at 360. Then, the CRT therapy is delivered using RF as calculated for Posture 1 when the patient is in Posture 1 and, if the patient changes posture, as indicated at 362, a different RF value is selected 364.

For example, the setup process may comprise calculating a separate RF value for a plurality of posture by, for example, requesting the patient to assume and hold different postures while the RF calculation process(es) described above are repeated for each posture. Then, with the patient ambulatory, one of the RF values is selected at any given time based on the sensed posture of the patient. For example, posture may be sensed using an accelerometer. If the patient assumes a posture for which a RF value has not been identified, the RF value used may be an average or median of the RF values for various postures, or a value of RF in the last posture sensed for which RF has been calculated, for example.

Figure 11:
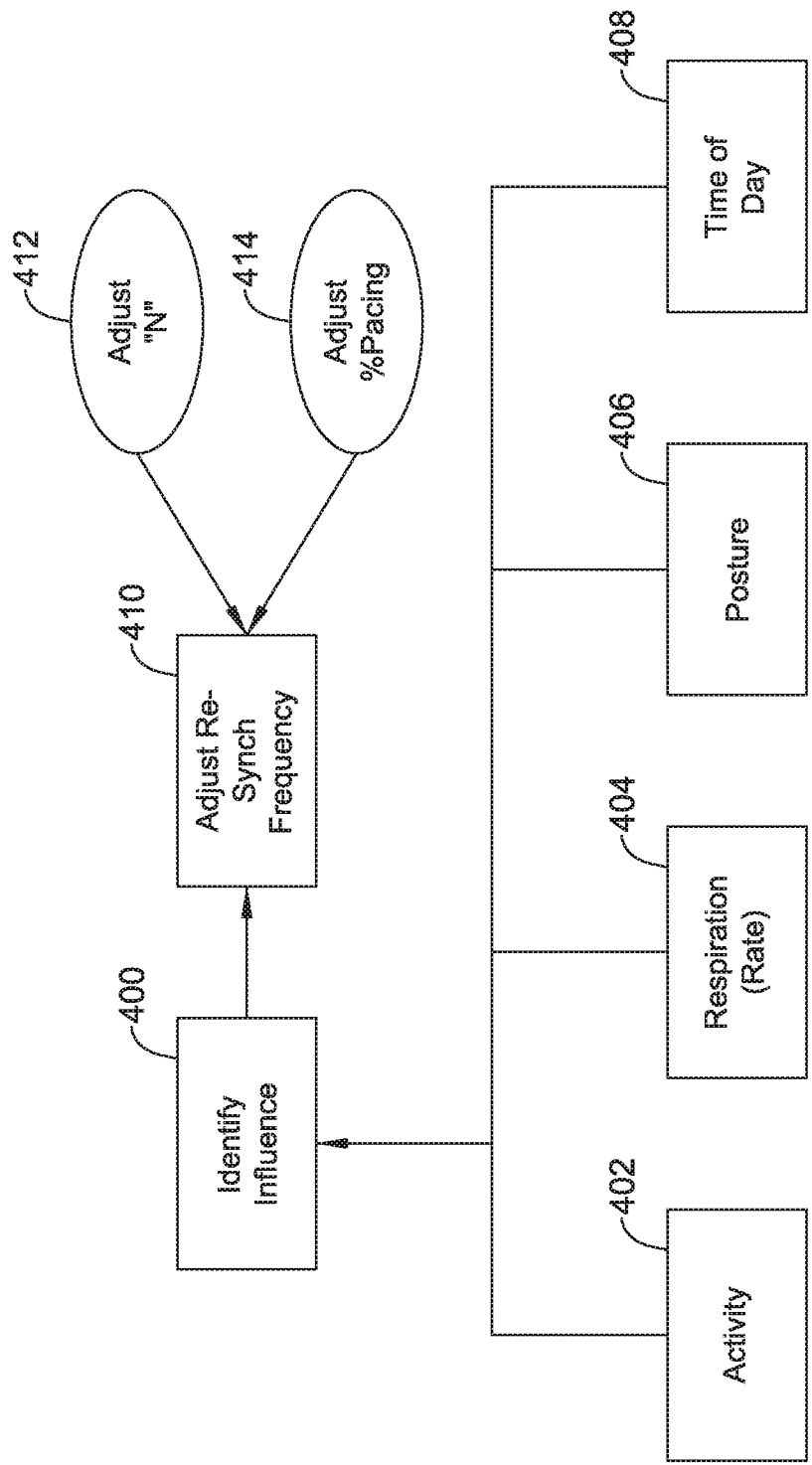

FIG. 11 shows another example. Here, the value for "N" is adjusted in response to sensed conditions that may influence PR drift as highlighted above in FIG. 8A. First, a relevant influence is identified as indicated at 400. Some illustrative influences may be activity of the patient 402 (particularly where the activity level of the patient changes), respiration 404 (particularly interested again in changes in the rate or depth of respiration, for example), posture 406 (for example a patient in repose is less likely to have a significant change of heart rate and therefore may be better suited to larger "N" than one who is standing and more likely to have a change in heart rate), and/or time of day 408 (nighttime, while the patient is sleeping, may work better for a larger "N" than daytime, while the patient is awake). If an influence 400 changes, then the resynchronization frequency is adjusted 410 by, for example, modifying "N" as indicated at 412 which will, in turn, adjust the percent pacing and percent therapy delivery 414. The method of FIG. 11 may be included as part of the adjustment step at 290 in FIG. 7. Some influences, such as a change in activity 402, respiration 404, or posture 406, may also be used to trigger an interrupt or error 280 in FIG. 7, truncating a CRT therapy set, if desired.

Figure 12:
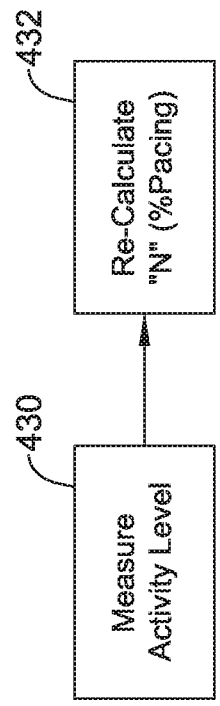
Figure 13:
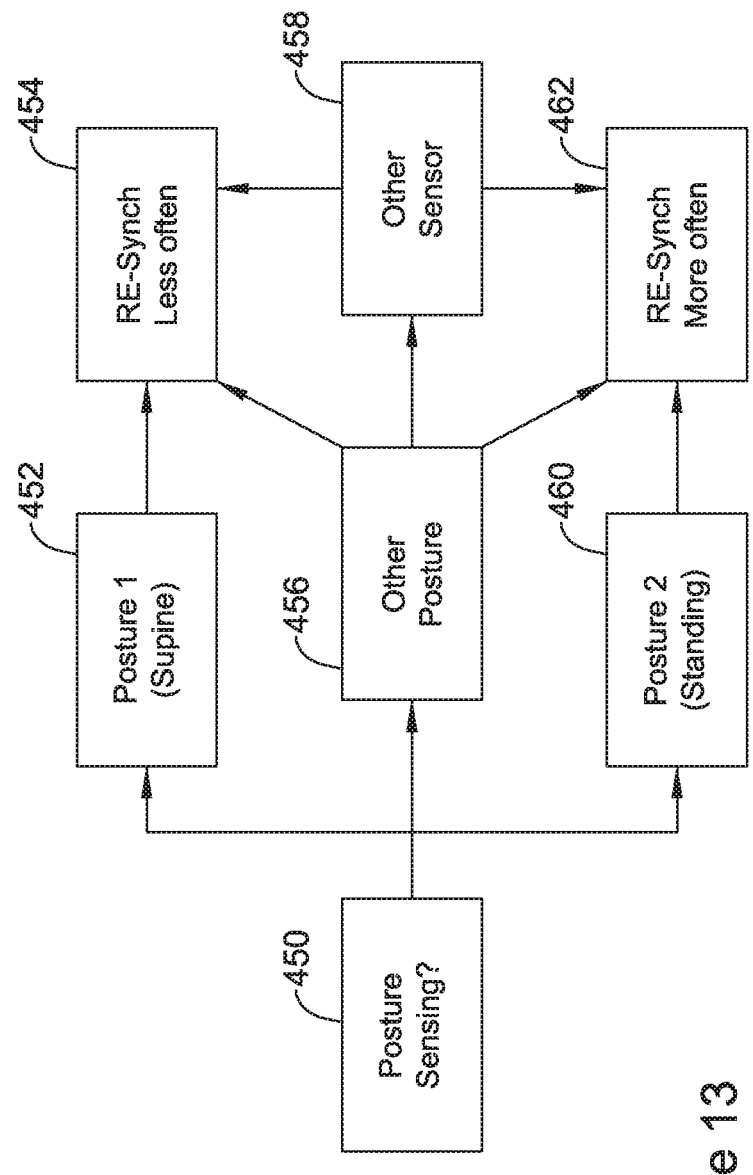

FIGS. 12 and 13 show particular examples of the concept of FIG. 11. In FIG. 12, the patient's activity level is measured at 430 using, for example, an accelerometer to detect patient movement or, alternatively, a temperature sensor on the LCP that can detect a change in blood temperature in the heart, which will also suggest a change in metabolic demand and patient activity. "N" is then calculated (or recalculated) in response to the measured activity level, as indicated at 432.

FIG. 13 shows another example using posture this time. Posture sensing is performed at 450 to yield one of three outcomes (in this example—most posture definitions may be used if desired in other examples). The three outcomes include Posture 1, supine, as indicated at 452, in which re-synchronization may be performed relatively less frequently as indicated at 454. The three outcomes also include Posture 2, standing, as indicated at 460, in which case the system uses a smaller N and resynchronizes more frequently, as indicated at 462, than if the patient was supine. For this example, any other posture may be handled at block 456, "Other Posture", in which case reference may be made to another sensor as indicated at 458 such as an activity sensor, which can then be used to determine whether to use a larger N and re-synch less often 454, or a smaller N and re-synch more often 462. For example, if the patient is active at block 458, then re-synchronization may be performed more often as the patient's heart rate is more likely to change quickly while active. In an alternative, the other posture block 456 may simply go to one or the other of blocks 454, 462 automatically.

In still another alternative, N may be set according to the measured cardiac rate to ensure a frequency per unit time of re-synchronization. For example, a patient with a heart rate of 60 beats per minute would take 22 seconds, approximately, to proceed through one full therapy regimen as shown in FIG. 7 (1 native interval at 1 second, 20 paced intervals at 1 second, and 1 paced interval at 1 second less a reduction due to RF). If the heart rate is 100 beats per minute, a full therapy regimen as shown in FIG. 7 would take about 13 seconds instead. Normalizing N by rate might mean, for example, setting N to ensure it is revisited every 20 seconds, making N=18 when the heart rate is 60 beats per minute, and N=31 when the heart rate is 100 beats per minute. Other approaches may be used instead to modify N in light of patient conditions.

Figure 14:
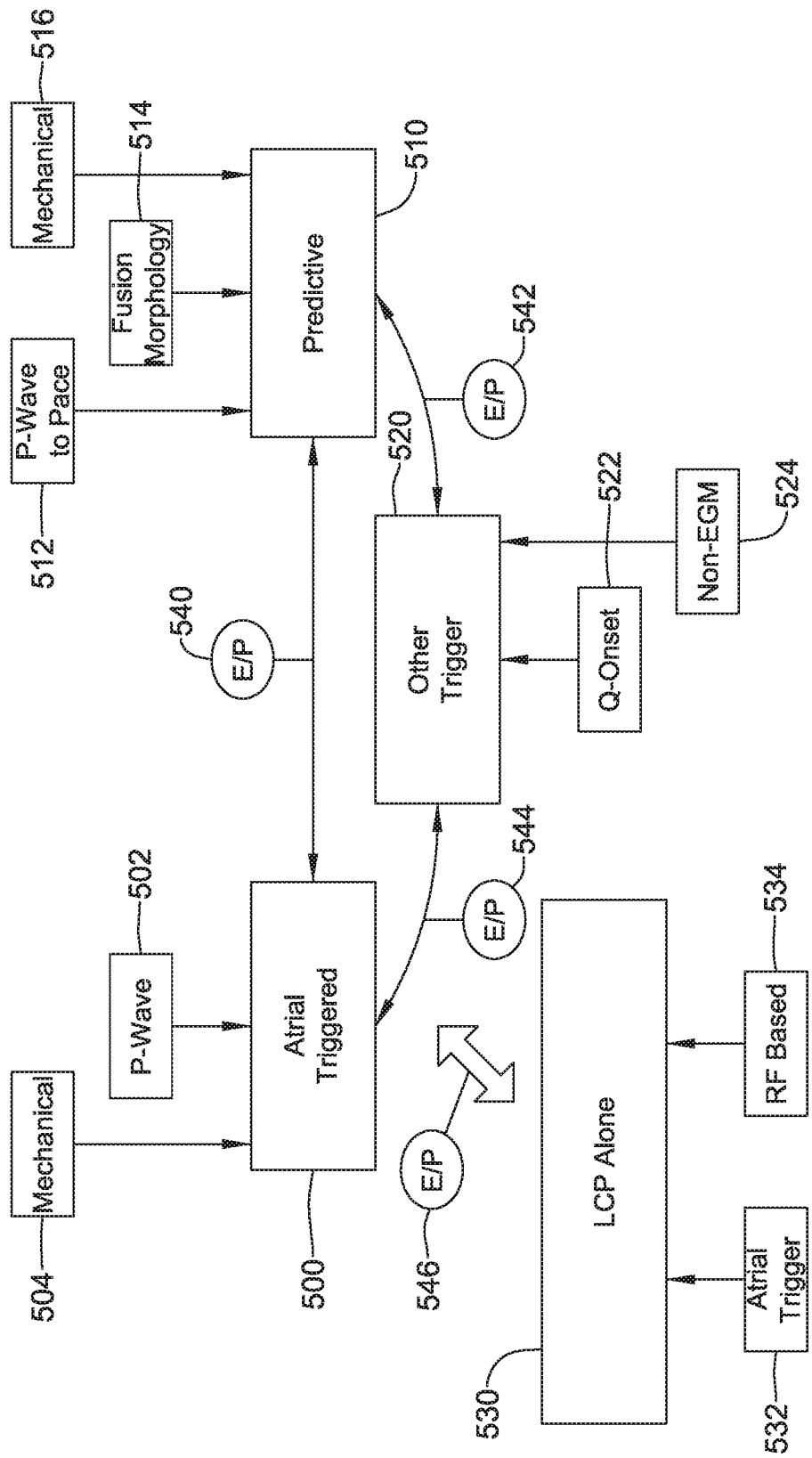
FIG. 14 shows in block form transitions among a number of different CRT methods.

FIG. 14 shows in block form transitions among a number of different CRT methods. While some examples are directed at using an LCP implanted in the LV to provide stand-alone CRT, such as a system shown in FIG. 1, above, other examples may be part of a broader method and system to provide a number of CRT solutions in one system. For example, an LCP may be implanted with one or more additional devices such as another LCP, a subcutaneous implantable monitor, or a subcutaneous implantable defibrillator, as shown in FIG. 3, above. In still further alternatives, a wearable apparatus, or a completely different apparatus, such as an implantable neuromodulation device, drug pump, or other apparatus, may be useful to provide data that can be helpful in providing CRT.

FIG. 14 illustrates mode switching among a plurality of pacing modes for CRT, with modes indicated at 500, 510, 520, and 530. Modes 500, 510, and 520 are each cooperative modes in which a left ventricular placed LCP delivers pace therapy and receives timing assistance from a second device such as an extracardiac device (SICD and/or SCM, for example) or a second LCP placed else wherein the heart, while mode 530 represents an independent mode of operation for the LCP, where the LCP itself determines pace timing for CRT.

For example, mode 500 is an atrial-triggered mode, which may use cardiac electrical information such as the P-wave, as indicated at 502. Alternatively, mechanical or other sensor information may be captured and used as a trigger, as indicated at 504, such as by identifying a heart sound, motion in the atrium, or pressure changes in the atrium or related to atrial activity.

Predictive mode 510 may operate by controlling a pace-to-pace interval and reviewing past result of pace therapy delivery to adjust the pace-to-pace interval based on a "prediction" of when will be the right time to deliver a next pace therapy. For example, a predictive mode may use analysis of prior P-wave to pace intervals, as indicated at 512, or may use a morphology assessment of a QRS complex to determine whether the QRS complex has a shape that indicates fusion 514, using for examples rules or templates in the analysis. In still further examples of predictive pacing 510, a mechanical signal, such as the timing of heart sounds in relative sequence, may be analyzed as indicated at 516 to optimize pace timing.

Other signals may be assessed as well, as indicated at 520, including a septal signal such as the Q-wave onset, as indicated at 522. Non-electrogram signals may be used, such as a heart sound emanating from other than the atria at 524.

An autonomous mode for CRT pacing by an LCP may be used as well, as indicated at 530. Such an LCP may be placed in the left ventricle, and may be capable of various analysis to help with triggered or predictive pacing management. For example, the LCP may monitor for an atrial trigger 532 such as a heart sound or an electrical signal such as the P-wave. The LCP may instead use an impedance measurement, triggering pacing when the volume reaches a threshold level or change. The LCP may detect motion such as movement in the atria and trigger therapy. The LCP may have a sensor for sensing heart sounds and may detect a sound associated with atrial or right ventricular contraction, to trigger therapy delivery. A pressure signal may monitored to detect changes indicating atrial or right ventricular contraction triggering therapy output. An electrical input may be used by filtering to obtain a far-field signal from the atrium, or the LCP may have a short lead accessing the atria and can sense atrial signals. Any of these inputs may instead be used in a predictive method that analyzes past results and modifies pace to pace timing to achieve desirable CRT in subsequent pace therapy delivery. Another option is to use the reduction factor (RF) based approach shown above in FIGS. 5-7, as indicated at 534.

As indicated by the various arrows, the example may switch from one mode to another. Such switching may be based on errors or preference (E/P) as indicated at any of 540, 542, 544, 546. Errors may indicate that a particular mode or mode type is unreliable at a given time, while preference may indicate the order in which modes are to be made available.

For example, an atrial triggered mode 500 may be in use, however, upon loss of the atrial signal (caused by posture change, arrhythmia, or unknown cause) may trigger switching to use of an "other" signal in block 520, or to use of a predictive mode as indicated at 510. In several examples, a preference for cooperative modes may be in place, with switching to mode 530 performed only after other modes 500, 510, 520 are shown unreliable or ineffective. In other examples, any of modes 500, 510, 520, 530 may be used at any time simply based on which is deemed to be most reliable and/or to provide the preferred quality of CRT.

An atrial triggered mode may include, for example, sensing an atrial contraction using an electrical or mechanical signal. See, for example, U.S. patent application Ser. No. 15/633,517, titled CARDIAC THERAPY SYSTEM USING SUBCUTANEOUSLY SENSED P-WAVES FOR RESYNCHRONIZATION PACING MANAGEMENT, and/or U.S. patent application Ser. No. 15/642,121, titled METHOD AND SYSTEM FOR DETERMINING AN ATRIAL CONTRACTION TIMING FIDUCIAL IN A LEADLESS CARDIAC PACEMAKER SYSTEM, the disclosures of which are incorporated herein by reference A predictive mode 510 may include, for example, monitoring evoked response(s) for fusion or comparing pace to R-wave (or other fiducial reference) timing to a target. See, for example, U.S. patent application Ser. No. 15/684,366, titled INTEGRATED MULTI-DEVICE CARDIAC RESYNCHRONIZATION THERAPY USING P-WAVE TO PACE TIMING, and/or U.S. patent application Ser. No. 15/684,264, titled CARDIAC RESYNCHRONIZATION USING FUSION PROMOTION FOR TIMING MANAGEMENT, the disclosures of which are incorporated herein by reference.

In addition, within the mode types, there may be multiple specific mode implementations such that a method or device can switch between modes of the same type. The assessment of different pacing modes, and switching between modes, may encompass the activation or deactivation of sensors and sensing capabilities specific to different modes. For example, an SICD or SCM may have multiple sensing channels and/or sense vectors that better target (using filtering or spatial differences) ventricular or atrial electrical signals. When a pacing mode relying on an electrical atrial signal is selected, the sense channel and/or sense vector best for atrial sensing may be activated; when a different pacing mode is selected, that same channel or vector may be deactivated to save power. A mechanical or optical sensor used in certain pacing modes may be deactivated when the relevant mode is not selected or under assessment.

Additional concepts related to switching between mode types for CRT using multiple cooperating devices may be found in U.S. patent application Ser. No. 15/710,118, titled MULTI-DEVICE CARDIAC RESYNCHRONIZATION THERAPY WITH MODE SWITCHING TIMING REFERENCE, the disclosure of which is incorporated herein by reference.

Figure 15:
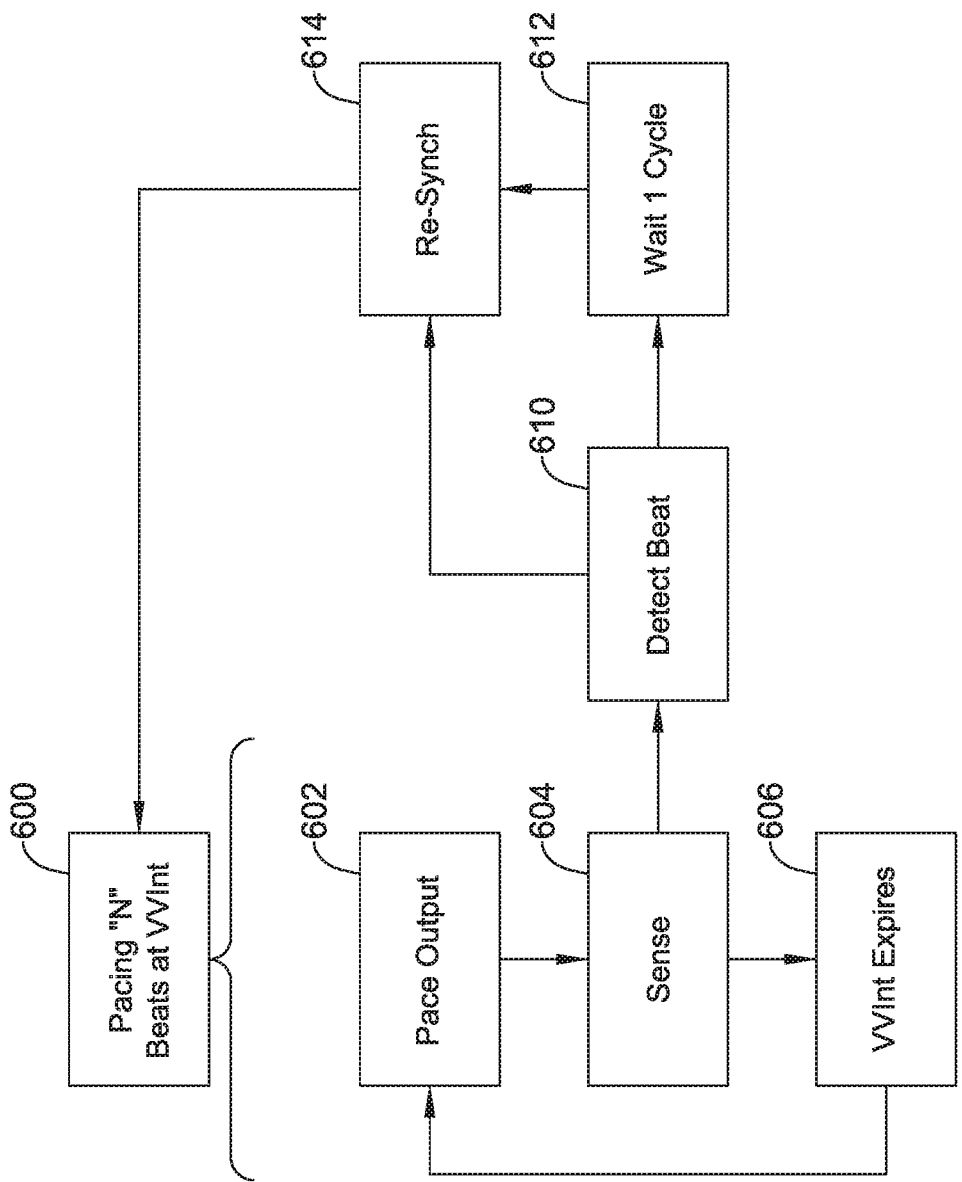
FIG. 15 illustrates a method of handling ventricular beats should those occur during CRT as illustrated by other methods herein.

FIG. 15 illustrates a method of handling ventricular beats should those occur during CRT as illustrated by other methods herein. The illustration presumes action during the step of pacing "N" eats at VVInt as indicated at 600. Within block 600 there are at least three substeps going on. A pace output occurs at 602 in which therapy is delivered. Sensing may be blanked or refractory during pace output, if desired, and then comes on in an interval between pace outputs, as indicated at 604. When VVInt expires, at 606, the pacing method iterates until N is reached (N being reached is not explicitly shown), as indicated by the line back to 602.

If during the sensing step 604 a beat is detected, the loop is exited at 610 upon beat detection. If a single beat is detected, the method may wait one additional cycle 612 and then performs synchronization again, as indicated at 614. The waiting of one additional cycle 612 is optional; the device may instead simply jump directly to re-synchronizing at 614. For example, in an embodiment that waits 1 cycle 612, a new VVInt may be measured for use in the re-started CRT regimen. Alternatively, the previously measured VVInt may be preserved and the system may jump directly to re-synchronizing by delivering the synchronizing pace (pace at an interval of the preserved VVInt as reduced by RF). The beat detection at 610 may further trigger assessment of any possible influences, such as shown in FIGS. 11-13 to see if the "N" value should be changed in light of the patient being in a likely variable rate state, or if a different RF value might be called for using a method as shown in FIGS. 9-10, prior to returning to the resynchronization pulse.

A series of illustrative and non-limiting examples follows. These examples are provided for further illumination and is should be understood that other embodiments using other combinations of features are also contemplated.

An illustrative and non-limiting example takes the form of a leadless cardiac pacemaker (LCP) configured for implantation entirely within a heart chamber of a patient or adjacent to a heart chamber of a patient (item 14 in FIG. 1, for example), the LCP comprising: a plurality of electrodes for therapy delivery and cardiac electrical sensing (items 64, 66, 68 in FIG. 2, for example); pacing means to generate pacing therapy outputs (pulse generator module 54 in FIG. 2, for example); and control means to control the use of the pacing means using signals sensed from the electrodes (processing module 60 in FIG. 2); wherein the control means is configured to provide cardiac resynchronization therapy (CRT) in sets using a predetermined reduction factor and a set parameter, "N", comprising delivering sets of CRT therapy including N pacing therapy outputs by: sensing a native R-R interval for the patient's heart (operational circuitry, dedicated circuitry, a defined state of a state machine, and/or stored instruction set for performing as shown at block 252 in FIG. 7); delivering a synchronization pace therapy at an interval, relative to a native ventricular event, calculated using the native R-R interval and the reduction factor (operational circuitry, dedicated circuitry, a defined state of a state machine, and/or stored instruction set for performing as shown at block 254 in FIG. 7, with PRX determined as indicated by either block 216 or blocks 224, 230 and 232 of FIG. 6); and delivering a plurality of additional pace therapies at intervals approximately equal to the native R-R interval (operational circuitry, dedicated circuitry, a defined state of a state machine, and/or stored instruction set for performing as shown at block 256 in FIG. 7, for example).

Additionally or alternative, the control means may be configured to provide the CRT without using an atrial sense reference, as described repeatedly above and using the methods illustrated in FIGS. 6-7.

Additionally or alternatively, the control means comprises initialization means configured to determine the reduction factor by: determining a PR interval for the patient's cardiac activity; and multiplying the PR interval by a variable, % PR, to calculate the reduction factor (such initialization means may include operational circuitry, dedicated circuitry, a defined state of a state machine, and/or stored instruction set for performing as shown in the calculated path 220, 224, 230, 232 in FIG. 6).

Additionally or alternatively, the control means may be configured to obtain % PR either by communication with an external programmer or from a stored value in the LCP (as indicated in the description of block 230 in FIG. 6, for example).

Additionally or alternatively, the control means comprises initialization means configured to determine the reduction factor by: sensing one or more native ventricular events to calculate an RR interval between native ventricular events and a PR interval within one or more native ventricular events; calculating a RR:PR ratio as a ratio of the RR interval to the PR interval; obtaining a variable, % PR, from memory or from an external programmer; and calculating the reduction factor as one minus the product of the first variable and the % PR; and further wherein the control means is configured to calculate the interval for the synchronization pace therapy by multiplying the reduction factor and the native beat interval. An example of this sort is explained above relative to FIG. 8A.

Additionally or alternatively, the control means may comprise initialization means configured to determine the reduction factor by: sensing one or more native ventricular events to calculate an RR interval between native ventricular events; communicating with a second device to determine when P-waves occurred in the one or more native ventricular events and calculating a PR interval; calculating a RR:PR ratio as a ratio of the RR interval to the PR interval; obtaining a variable, % PR, from memory or from an external programmer; and calculating the reduction factor as one minus the product of the first variable and the % PR; and further wherein the control means is configured to calculate the interval for the synchronization pace therapy by multiplying the reduction factor and the native beat interval. An example of this sort is explained above relative to FIG. 8A.

Additionally or alternatively, the LCP may further comprise a patient status monitoring means, and the control means is configured to make adjustments to the CRT including: using the patient status monitoring means to monitor a patient condition that would influence the reduction factor; detecting a change in the patient condition; and adjusting the reduction factor. For example, FIG. 9 shows an example where the control means identifies an autonomic influence, and replaces the reduction factor with a different value.

Additionally or alternatively, the LCP may be configured such that the status monitoring means comprises a posture sensor and the patient condition is a posture of the patient, such that the control means is configured to adjust the reduction factor in response to finding that the patient has changed postures. For example, FIG. 10 shows an example in which the control means identifies a reduction factor for a first posture, detects a change in posture, and replaces the reduction factor with a different value.

Additionally or alternatively, the LCP may comprise a patient status monitoring means, and the control means is configured to make adjustments to the CRT including: sensing for a predetermined patient condition that may influence PR interval; and in response to sensing the predetermined patient condition, adjusting "N". An example is shown in FIG. 11, in which a plurality of patient status means are identified including activity sensor 402, or respiration sensor 404, or posture sensor 406, or time of day determiner 408, any of which can be used by the control means (embodied as dedicated circuitry, a state machine, or controller acting on stored instructions, or a combination thereof) to operate as illustrated at block 400 and 410.

Additionally or alternatively, the LCP may comprise a posture sensor, wherein the control means is configured to monitor patient status and make adjustments to the CRT including: using the posture sensor to monitor a posture of the patient; determining that the patient has changed postures between standing and one of sitting or laying down; and: if the patient has gone from standing to sitting or laying down, increasing "N"; or if the patient has gone from sitting or laying down to standing, reducing "N". For example, FIG. 11 shows a posture sensor 406 as one of the means that a control means may rely upon to adjust the resynchronization frequency, with a specific example further detailed by FIG. 13 with reference to laying down 452 (such as supine posture) and standing up 460.

Additionally or alternatively, the LCP control means may be configured to iteratively provide the CRT in sets of N pacing pulses and to adjust N after delivery of a plurality of sets of N pacing pulses by: observing changes in native R-R intervals measured prior to delivery of the synchronization pace therapy in the plurality of sets, to calculate an R-R drift; and adjusting N using the calculated drift. An example of such a control means is described above relative to block 346 of FIG. 8B.

Additionally or alternatively, the LCP may further comprise communication means (FIG. 2, block 52) for communicating with a second medical device; wherein the control means is configured for at least first and second modes of CRT therapy wherein: the first mode comprises delivering sets of CRT therapy including N pacing therapy outputs via the combination of sensing a native R-R interval, delivering a synchronization pace therapy, and delivering a plurality of additional pace therapies, as recited in any of the preceding illustrative examples; and the second mode comprises using the communication means to obtain atrial event timing information from a second implantable or wearable medical device to control or optimize pace therapy timing. FIG. 14 illustrates multiple modes available for stand-alone LCP operation (530) and cooperative operation (510, 520, 530), including a specific reduction factor based method indicated at 534 which may take the form as shown in FIGS. 6-7, above.

Additionally or alternatively, an implantable medical device system comprising at least a leadless cardiac pacemaker (LCP) as in these illustrative examples, and a second implantable medical device, the LCP and the second implantable medical device configured for communicating with one another, wherein the system is configured to provide cardiac resynchronization therapy (CRT) in at least first and second approaches as follows: the first approach calls for the LCP to perform the first mode; and the second approach calls for the LCP and the second implantable medical device to cooperatively implement the second mode. FIG. 3 shows an example wherein a patient has multiple implanted devices configured to operate cooperatively in one or more modes, and FIG. 14 illustrates multiple modes available for stand-alone LCP operation (530) and cooperative operation (510, 520, 530), including a specific reduction factor based method indicated at 534 which may take the form as shown in FIGS. 6-7, above.

Additionally or alternatively, an LCP or a system as in any of these illustrative examples may be configured such that the control means comprises a state machine.

Additionally or alternatively, an LCP or a system as in any of these illustrative examples may be configured such that the control means comprises a microcontroller and memory storing executable instructions for the microcontroller.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A leadless cardiac pacemaker (LCP) configured for implantation entirely within a heart chamber of a patient or adjacent to a heart chamber of a patient, the LCP comprising:
   a plurality of electrodes for cardiac therapy delivery and cardiac electrical sensing;
   pacing circuitry configured to generate pacing therapy outputs; and
   control circuitry configured to analyze signals from the electrodes and to control the use of the pacing circuitry for cardiac resynchronization therapy (CRT);

wherein the control circuitry is configured for:
sensing a native R-R interval from the patient's heart;
calculating a synchronization interval by reducing the native R-R interval using a reduction factor;
sensing a native ventricular event;
delivering a synchronization pace therapy upon expiration of the synchronization interval following the native ventricular event; and
delivering a predetermined number, N, of additional pace therapies at intervals approximately equal to the native R-R interval.

2. The LCP of claim 1, wherein the control circuitry is configured to provide the CRT without using an atrial sense reference.

3. The LCP of claim 1, wherein the control circuitry is configured to perform an initialization of CRT to determine the reduction factor by:
determining a PR interval for the patient's cardiac activity; and
multiplying the PR interval by a variable, % PR, to calculate the reduction factor.

4. The LCP of claim 1, wherein the control circuitry is configured to perform an initialization of CRT to determine the reduction factor by:
sensing one or more native ventricular events to calculate an RR interval between native ventricular events and a PR interval within one or more native ventricular events;
calculating a RR:PR ratio as a ratio of the RR interval to the PR interval;
obtaining a variable, % PR, from memory or from an external programmer; and
calculating the reduction factor as one minus the product of the first variable and the % PR; and
further wherein the control circuitry is configured to calculate the synchronization interval by multiplying the reduction factor and the native beat interval.

5. The LCP of claim 1, wherein the control circuitry is configured to perform an initialization of CRT to determine the reduction factor by:
sensing one or more native ventricular events to calculate an RR interval between native ventricular events;
communicating with a second device to determine when P-waves occurred in the one or more native ventricular events and calculating a PR interval;
calculating a RR:PR ratio as a ratio of the RR interval to the PR interval;
obtaining a variable, % PR, from memory or from an external programmer; and
calculating the reduction factor as one minus the product of the first variable and the % PR; and
further wherein the control circuitry is configured to calculate the synchronization interval by multiplying the reduction factor and the native beat interval.

6. The LCP of claim 1, wherein the control circuitry is configured to monitor patient status and make adjustments to the CRT including:
sensing for a patient condition that would influence the reduction factor;
detecting a change in the patient condition; and
adjusting the reduction factor.

7. The LCP of claim 1, further comprising a posture sensor, wherein the control circuitry is configured to monitor patient posture and make adjustments to the CRT including:
sensing a posture of the patient;
determining whether the patient has changed postures; and
in response to finding that the patient has changed postures, adjusting the reduction factor.

8. The LCP of claim 1, wherein the control circuitry is configured to monitor patient status and make adjustments to the CRT including sensing for a predetermined patient condition that may influence PR interval, and in response to sensing the predetermined patient condition, adjusting "N".

9. The LCP of claim 1, further comprising a posture sensor, wherein the control circuitry is configured to monitor patient posture and make adjustments to the CRT including:
sensing a posture of the patient;
determining that the patient has changed postures between standing and one of sitting or laying down; and:
if the patient has gone from standing to sitting or laying down, increasing "N"; or
if the patient has gone from sitting or laying down to standing, reducing "N".

10. The LCP of claim 1, wherein the control circuitry is configured to iteratively provide the CRT in sets and to adjust N after delivery of a plurality of sets by:
observing changes in native R-R intervals, to calculate an R-R drift; and
calculating N using the calculated drift.

11. The LCP of claim 1, wherein the control circuitry is configured for at least first and second modes of CRT therapy wherein:
the first mode comprises delivering sets of CRT therapy via the combination of sensing a native R-R interval, delivering a synchronization pace therapy, and delivering a plurality of additional pace therapies;
the second mode comprises obtaining atrial event timing information from a second implantable or wearable medical device to control or optimize pace therapy timing.

* * * * *